(12) United States Patent
de Juan, Jr. et al.

(10) Patent No.: US 7,077,848 B1
(45) Date of Patent: Jul. 18, 2006

(54) SUTURELESS OCCULAR SURGICAL METHODS AND INSTRUMENTS FOR USE IN SUCH METHODS

(75) Inventors: Eugene de Juan, Jr., Phoenix, MD (US); Terry H. Shelley, Hampstead, MD (US); Aaron C. Barnes, Columbia, MD (US); Patrick S. Jensen, Cockeysville, MD (US)

(73) Assignee: John Hopkins University, Baltimore, MD (US)

( * ) Notice: Subject to any disclaimer, the term of this patent is extended or adjusted under 35 U.S.C. 154(b) by 0 days.

(21) Appl. No.: 09/523,767

(22) Filed: Mar. 11, 2000

(51) Int. Cl.
*A61F 11/00* (2006.01)

(52) U.S. Cl. ...................... 606/108; 606/166
(58) Field of Classification Search .............. 606/166, 606/107, 108, 169; 604/22–24, 26, 21, 289, 604/294, 296; 623/905
See application file for complete search history.

(56) References Cited

U.S. PATENT DOCUMENTS

| | | | |
|---|---|---|---|
| 3,618,594 A | * | 11/1971 | Banko ...................... 606/107 |
| 3,659,607 A | | 5/1972 | Banko |
| 3,868,957 A | | 3/1975 | Doddington |
| 3,884,237 A | | 5/1975 | O'Malley et al. ........ 128/303.1 |
| 4,258,716 A | | 3/1981 | Sutherland |

(Continued)

FOREIGN PATENT DOCUMENTS

DE 196 37 093 A1 3/1998

(Continued)

OTHER PUBLICATIONS

E. de Juan et al., *Retina*, 9(4):258-262 (1989).

(Continued)

*Primary Examiner*—Eduardo C. Robert
*Assistant Examiner*—Jessica R. Baxter
(74) *Attorney, Agent, or Firm*—Peter F. Corless; William J. Daley, Jr.; Edwards Angell Palmer & Dodge LLP

(57) ABSTRACT

Featured are new methods for performing intra-ocular surgery that allow surgical personnel to access the intra-ocular volume to perform a surgical procedure or technique but which does not require the use of sutures to seal the sclera and/or conjunctiva following the procedure. The methods of the present invention generally include providing an entry alignment device and inserting the entry alignment device into an eye through both the conjunctiva and sclera so as to form an entry aperture that extends between the exterior of the eye and the intra-ocular volume within the eye. The provided alignment device is configured so as to form or provide an aperture or opening in each of the conjunctiva and sclera of the eye and to maintain these apertures or openings in each of the conjunctiva and sclera aligned during the surgical procedure so these apertures or openings form the entry aperture. In more particular aspects, the provided entry alignment device is sized such that when the entry alignment device is removed from the eye following the completion of the surgical procedure, the aperture or opening formed in the sclera seals without the use of sutures. In a more specific aspect of the present invention, the provided entry alignment device is sized such that the apertures or openings and thus the entry aperture are self sealing. In other embodiments, a plurality of entry alignment devices are provided so a plurality of entry apertures can be formed in the eye. The invention also features a high speed vitreous cutting and aspirating device particularly configured for use in such methods and surgical procedures and techniques as well as the related entry alignment devices and other surgical instruments.

48 Claims, 10 Drawing Sheets

U.S. PATENT DOCUMENTS

| | | | |
|---|---|---|---|
| 4,650,460 A | | 3/1987 | Roizenblatt .................. 604/128 |
| 4,692,142 A | * | 9/1987 | Dignam et al. ............. 604/117 |
| 5,318,040 A | | 6/1994 | Kensey et al. |
| 5,487,725 A | | 1/1996 | Peyman ....................... 604/604 |
| 5,547,473 A | * | 8/1996 | Peyman ....................... 604/22 |
| 5,676,669 A | * | 10/1997 | Colvard ....................... 623/905 |
| 5,807,244 A | | 9/1998 | Barot |
| 5,817,099 A | * | 10/1998 | Skolik et al. .................. 604/22 |
| 5,865,831 A | * | 2/1999 | Cozean et al. .................. 606/6 |
| 5,919,158 A | * | 7/1999 | Saperstein et al. .......... 623/905 |
| 5,941,250 A | * | 8/1999 | Aramant et al. ............. 623/905 |
| 5,989,262 A | | 11/1999 | Josephberg |
| 5,997,498 A | | 12/1999 | de Juan, Jr. ............... 604/26 |
| 6,059,792 A | | 5/2000 | Josephberg |
| 6,378,526 B1 | * | 4/2002 | Bowman et al. ............ 128/898 |

FOREIGN PATENT DOCUMENTS

| | | |
|---|---|---|
| WO | WO 93/05719 | 4/1993 |
| WO | WO 97/47247 | 12/1997 |
| WO | WO 01/15640 A1 | 3/2001 |

OTHER PUBLICATIONS

J. Khadem et al., *IOVS*, 40(13):3132-3137 (1999).

A. Trott, *JAMA*, 277(19) 1997).

E. de Juan et al., *American Journal of Ophthalmology*, 109:218-220 (1990).

D. Broadway et al., *American Journal of Ophthalmology*, 125(6):805-818 (1998) (Abstract).

Surgical Techniques for Repositioning a Dislocaed Intraocular Lens, Repair of Iridodialysis, and Secondary Intraocular Lens Implantation Using Innovative 25-Gauge Forceps; S. Chang, et al.; American Journal of Opthalmology, vol. 119, No. 2, pp. 165-174; Feb. 1995.

* cited by examiner

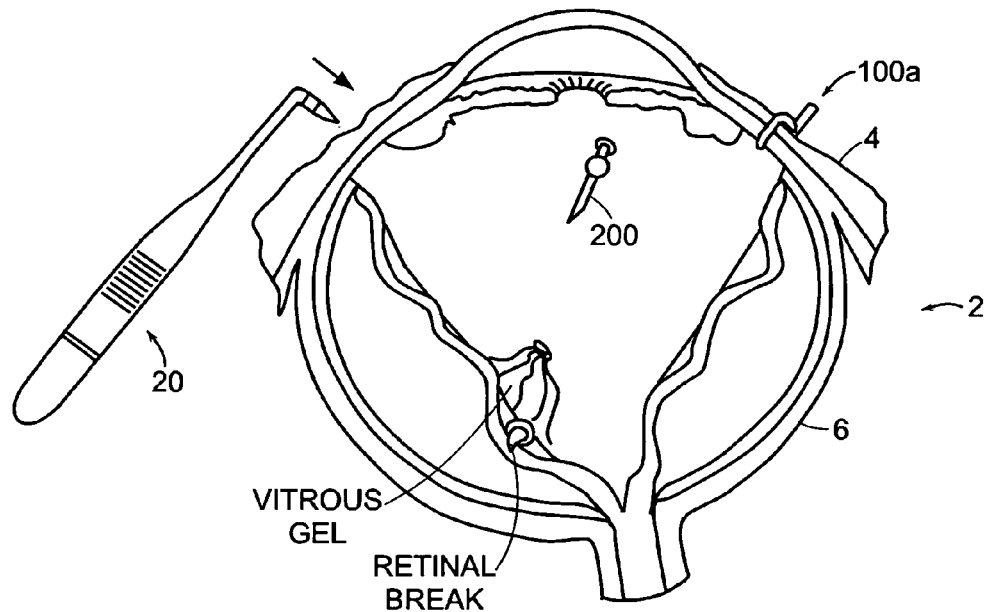
FIG. 2
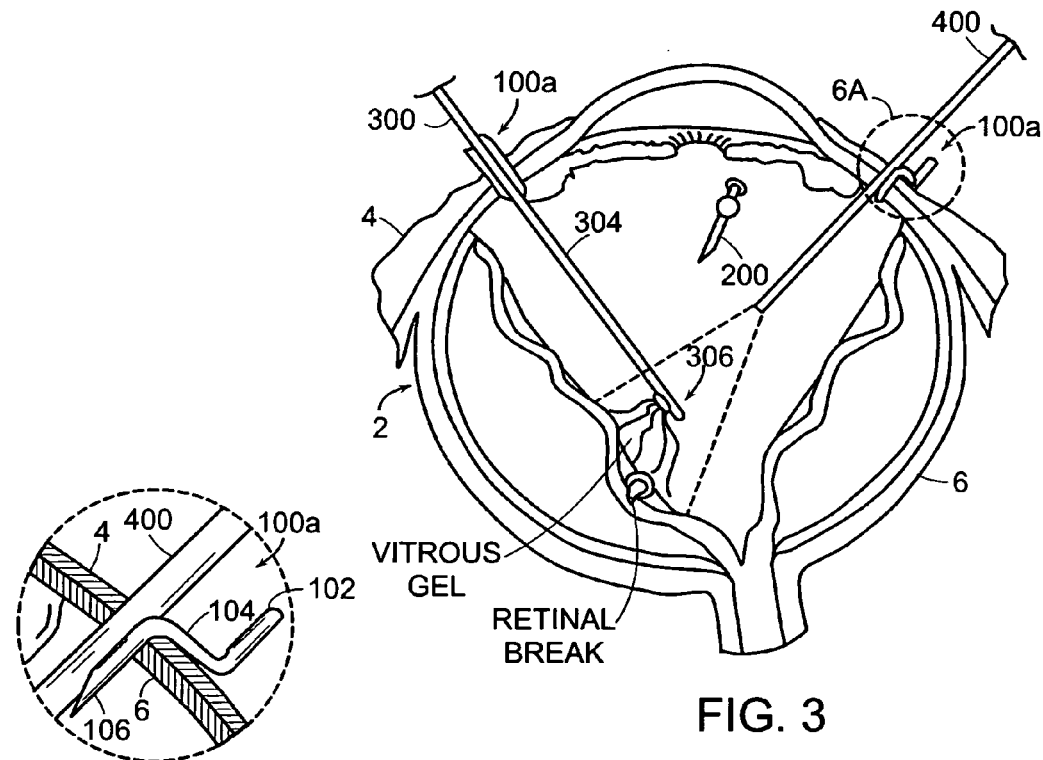
FIG. 6A
FIG. 3

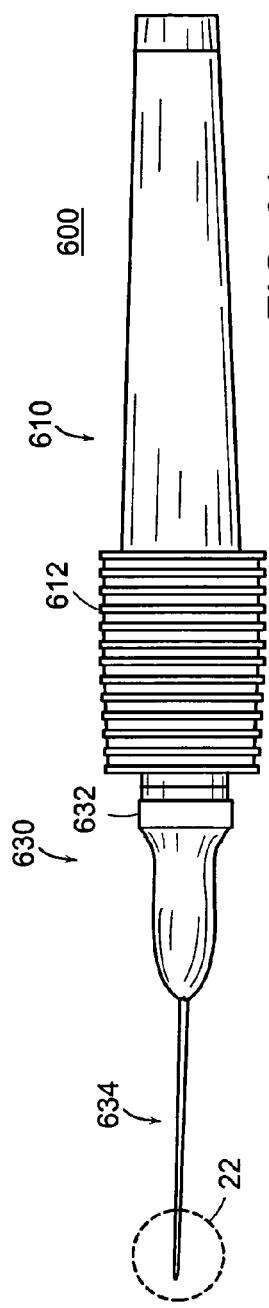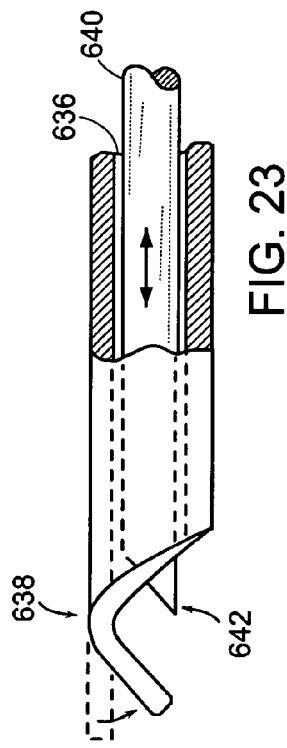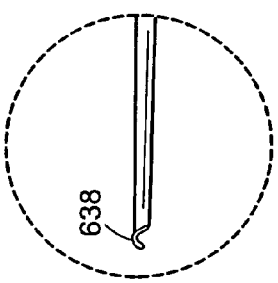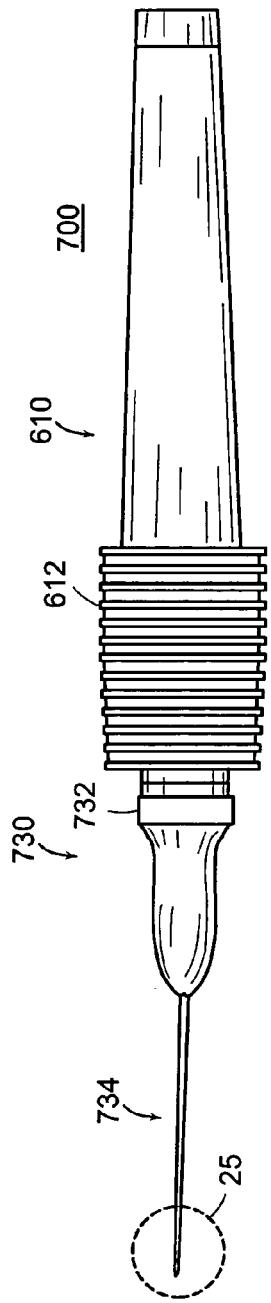

SUTURELESS OCCULAR SURGICAL METHODS AND INSTRUMENTS FOR USE IN SUCH METHODS

FIELD OF INVENTION

The present invention relates to methods for performing surgery and instruments used therewith, in particular sutureless surgical methods and techniques and the instrumentalities therefor which do not involve the use of sutures to seal the openings through which the instrumentalities are inserted, and more particularly, to surgical methods involving the eye (e.g., retinal tear or detachment surgery, macular hole surgery) as well as the instruments or devices used during such surgical procedures, where the openings in the eye provided for the use of the instruments need not be sealed by suturing.

BACKGROUND OF THE INVENTION

Retinal tears can occur when the vitreous, a clear gel-like substance that fills the center of the eye, pulls away from the retina thereby leaving behind a tear or hole in the retina. Rhegmatogenous retinal detachments can result if the retinal breaks (i.e., tears or holes in the retina) are not treated. With retinal breaks, fluid from the vitreous apparently seeps through the retinal break and accumulates under the retina. The degree of detachment is measured by the volume of subretinal fluid present as well as the area of the retina involved. Some symptoms of retinal detachment include the presence of floaters, flashes, shadows or blind areas, decreased visual acuity and metamorphopsia.

A number of techniques may be employed for treating retinal detachments, including using a scleral buckle, pneumatic retinopexy, cryopexy (i.e., freezing) and photocoagulation using a laser or xenon arc light source. These techniques may be used alone or in combination with each other to treat the retinal detachments. For example, a combination of a scleral buckle and photocoagulation may be used in some cases. Alternatively, retinal tears with little or no nearby detachment may be treated using photocoagulation or cryopexy.

Current vitreoretinal techniques in which surgical instruments are inserted into the eye require the dissection of the conjunctiva 4 and the creation of pars plana scleral incisions through the sclera 6. As more clearly illustrated in FIG. 1, the dissection of the conjunctiva typically involves pulling back the conjunctiva 4 about the eye 2 so as to expose large areas of the sclera 6 and the clipping or securing of the conjunctiva in that pulled back state (normal position of conjunctiva shown in phantom). In other words, the sclera 6 is not exposed only in the areas where the pars plana scleral incisions are to be made. As discussed below the area of the sclera 6 through which the infusion cannula would be inserted also would be exposed.

Following the creation of the incisions, surgical instruments are passed through these incisions and the inserted instruments are observed through the pupil using a microscope and corrective optics. These instruments are used to manipulate and/or dissect retinal tissues within the eye as well as to implement the specific retinal treatment technique (e.g., photocoagulation). The scleral incisions created for vitreoretinal surgery are made large enough to accommodate the required instruments, the inserted portions being typically 19 or 20 gauge (approximately 1 mm) in diameter.

For example, using a laser in the photocoagulation technique, an instrument capable of transmitting bursts of laser light is inserted into the eye and the retinal break is surrounded with one or more rows of a plurality of laser burns or laser heat spots. These laser burns or heat spots produce scars which prevent fluid from passing through and collecting under the retina. In the photocoagulation procedure, a gas is exchanged with the vitreous fluid being aspirated from within the eye so that the gas is intraocular when performing photocoagulation.

During vitreoretinal surgery, intraocular pressure is maintained by infusing a fluid, such as a buffered saline solution, from an elevated IV bottle into the eye through a cannula. Often the surgical procedures will call for air to be infused through the cannula while the fluid is being drained and/or aspirated through a second port or means. Such a cannula also is passed through an incision or is inserted through the sclera 6 by a trocar.

After completing the specific treatment procedure, the inserted instruments are removed from the incisions in the sclera. Because the incisions through the sclera are large enough to pass 19 or 20 gauge instruments, the incisions are typically too large to self-seal. Thus, the incisions must be sutured shut. Similarly, the infusion cannula is removed from the sclera and the opening or incision in the sclera 6 for the cannula also is sutured shut. Following the suturing of the scleral incisions, the surgical personnel reposition the conjunctiva in its normal position and reattach the free end(s) of the conjunctiva to the eye 2 using sutures.

While such methods and techniques have proven to be effective in the treatment of vitreoretinal disease, there is a strong motivation to move away from procedures requiring sutures and instead look to greatly simplified sutureless procedures. Thus, it would be desirable to have improved and novel methods to perform such sutureless procedures that would be simpler as compared to prior art methods or techniques as well as to provide improved surgical instruments that are useable during such sutureless procedures and which preferably would be no more difficult to use than existing prior art devices. Such sutureless procedures would preferably be less costly and less intrusive as compared to prior art procedures.

SUMMARY OF THE INVENTION

We have now produced new methods for performing intra-ocular surgery that allow surgical personnel to access the intra-ocular volume (i.e., the interior of the eye) to perform a surgical procedure or technique but which does not require the use of sutures to seal the sclera and/or conjunctiva following the procedure. In more particular aspects of the invention, these methods leave the sclera and/or conjunctiva in a condition following the surgical procedure such that the tissues thereof can seal openings made therein for purposes of performing the intra-ocular surgical procedure. More specifically featured are methods for treating a retinal tear or retinal detachment. The invention also provides the related entry alignment devices and surgical instruments for use in connection with such methods and surgical procedures or techniques.

The methods of the present invention generally comprise providing an entry alignment device and inserting the entry alignment device into an eye through both the conjunctiva and sclera so as to form an entry aperture that extends between the exterior of the eye and the intra-ocular volume within the eye. The entry alignment device being provided is configured so as to form or provide an aperture or opening in each of the conjunctiva and sclera of the eye and to maintain these apertures or openings in each of the conjunctiva and sclera aligned during the surgical procedure so these apertures or openings form the entry aperture.

In more particular aspects, the entry alignment device being provided is sized such that when the entry alignment device is removed from the eye following the completion of the surgical procedure, the apertures or openings formed in the conjunctiva and sclera, and thus the entry aperture, are sealed without the use of sutures. In a more specific aspect of the present invention, the entry alignment device being provided is sized such that when the entry alignment device is removed from the eye, the apertures or openings and thus the entry aperture are self sealing.

According to additional aspects of the present invention, the methods further include providing a plurality of entry alignment devices and inserting each of the plurality of entry alignment devices through the conjunctiva and sclera so as to form a plurality of entry apertures. Additionally, such methods further include providing a surgical instrument having an operable end for insertion through the entry aperture, a portion of the operable end having a cross-sectional diameter not greater than 25 gauge; and inserting the surgical instrument through the entry apertures into the eye. Such surgical instruments include a high-speed vitreous cutter, forceps, scissors, pick, light source, laser light source, fragmentation device, aspirator and a diathermy device or other treatment device as is known in the art.

Also, an infusion cannula can be provided that has an operable end for insertion into the eye namely through the conjunctiva and the sclera. The operable end preferably has a cross-sectional diameter of not more than 25 gauge and is interconnected to an infusion source. The operable end of such a cannula also is inserted through the conjunctiva and sclera so that fluids such as a gas, can be infused into the eye typically during an eye surgical procedure. Preferably the infusion cannula is a non-traumatic cannula, such as that described in U.S. Ser. No. 09/366,914 the teachings of which are incorporated herein by reference, that minimizes damage to the retina. Also an infusion source contemplated for use with the methods of the present invention includes an in-line humidifier, as described in U.S. Pat. No. 5,997,498 the teachings of which are incorporated herein by reference, so that the gas being infused is humidified.

As indicated above, the entry alignment devices are generally configured so as to form or provide an aperture or opening in each of the conjunctiva and sclera of the eye and to maintain these apertures or openings aligned during the surgical procedure so these apertures or openings form an entry aperture extending between the exterior of the eye and the intra-ocular volume. The present invention features a number of such entry alignment devices including, but not limited to, a metal cannula, a polyimide cannula, a wire spreader and a shoe-horn style member that are more particularly described below. Some of these entry alignment devices, such as the cannula style of devices, are configured so as to include a lumen that extends between the exterior of the eye and the intra-ocular volume when the device is inserted into the eye. Thus, for this type of entry alignment device the lumen forms the entry aperture and the surgical instruments are inserted through the lumen. Other of the entry alignment devices, such as the wire spreader and the shoe-horn style member, are configured so as to spread apart at least some of the tissue of the conjunctiva and sclera about the entry aperture so as to form an opening in which the surgical instruments can be inserted, which opening would expand outwardly as the instrument is inserted therein.

Also featured are alignment device insertion tools and a high speed vitreous cutting and aspiration device. The insertion tools are used in conjunction with the entry alignment device to form a trocar to facilitate insertion of the entry alignment device through the conjunctiva and the sclera and to facilitate the formation of an entry aperture. The high speed cutting and aspiration device is particularly configured so that it is capable of cutting and aspirating vitreous material from the intra-ocular volume when the operable end of this device is sized so as to have a cross-sectional diameter of 25 gauge or less. Additionally featured are other surgical instruments discussed below for use with such entry alignment devices.

Other aspects and embodiments of the invention are discussed below.

BRIEF DESCRIPTION OF THE DRAWING

For a fuller understanding of the nature and desired objects of the present invention, reference is made to the following detailed description taken in conjunction with the accompanying drawing figures wherein like reference character denote corresponding parts throughout the several views and wherein:

FIGS. 2–5 are cross-sectional schematic views of an eye undergoing a transconjunctival sutureless vitreoretinal procedure embodying the methodology of the present invention;

FIG. 6A is an expanded schematic view of a portion of FIG. 3;

FIGS. 21–23 are various views of a forceps according to the present invention;

FIGS. 24–25 are various views of a cutting instrument according to the present invention;

DESCRIPTION OF THE PREFERRED EMBODIMENT

Figure 1:
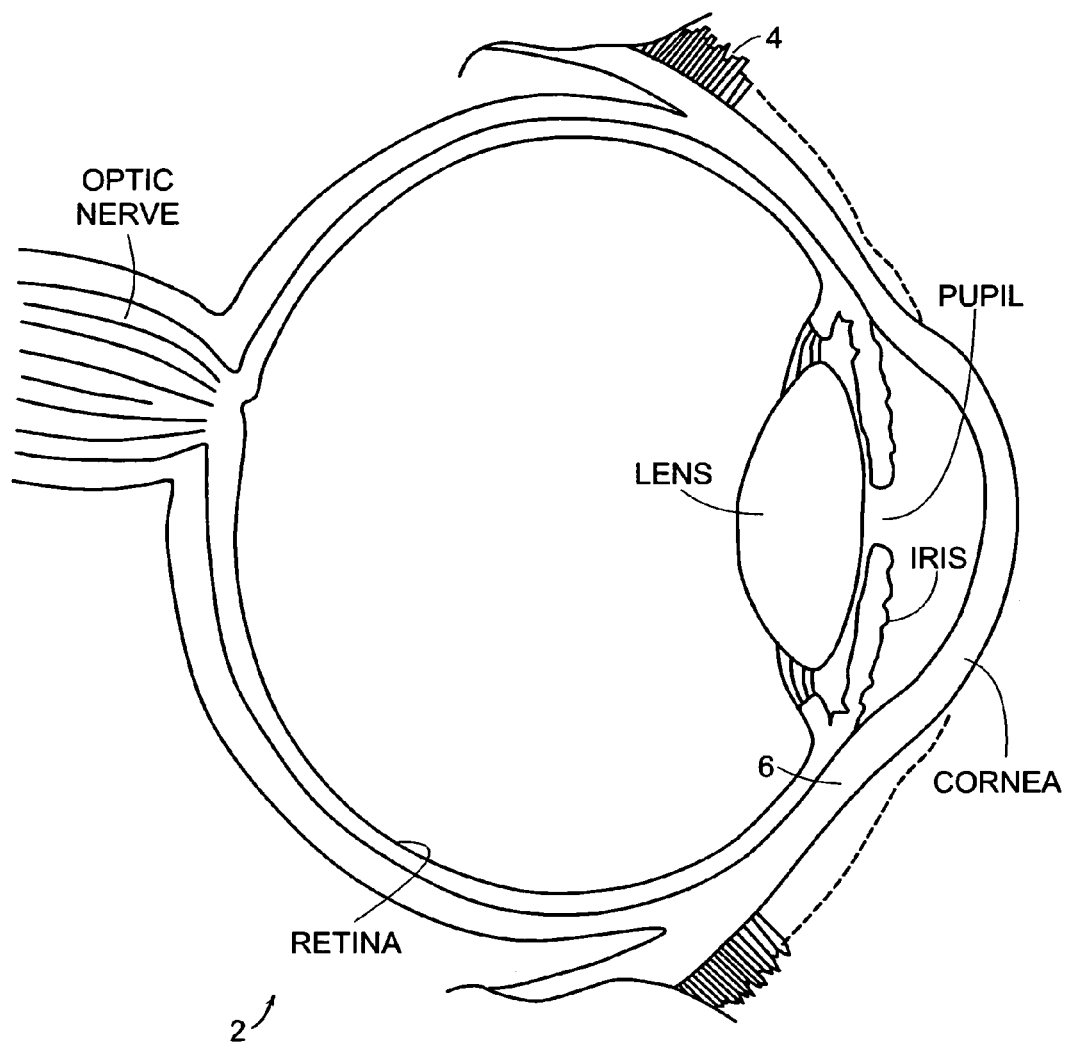
FIG. 1 is a cross-sectional schematic view of a non-diseased eye illustrating the prior art technique of pulling back of the conjunctiva.

Referring now to the various figures of the drawing wherein like reference characters refer to like parts, there is shown in FIGS. 2–5 cross-sectional schematic view of an eye undergoing a transconjunctival sutureless vitreoretinal surgical procedure that embodies the methodology of the present invention and expanded local views of the schematic views are provided in FIGS. 6A,B. Although the following describes the methodology of the present invention in terms of a vitreoretinal surgical procedure, it should be recognized that other surgical procedures can adapt the methodology of the present invention so as to yield other type of sutureless surgical procedures, such other surgical procedures includes, but is not limited to fluid gas exchange, vitreous hemorrhage, vitrectomy, macular hole and diabetic membrane peeling. Additionally, the surgical procedures includes procedures performed on adults as well as pediatric applications. Reference also should be made to the FIGS. 7–28 for any elements or features not otherwise shown in FIGS. 2–6.

As preparation, the surgical personnel typically sterilize the eyeball as well as performing other actions that otherwise prepare a given eye 2 for the surgical procedure to be performed. After preparing the eye 2 for the surgical procedure, the surgical personnel generally would grasp an entry alignment device according to the present invention with a pair of forceps or tweezers 20 or mount the entry alignment device upon an insertion tool such as those shown in FIGS. 13–16. After grasping the entry alignment device or mounting the entry alignment device upon an insertion tool, the surgeon would insert the entry alignment device into the eyeball. This insertion procedure is repeated as needed to insert the number of entry alignment devices required to meet the needs of a given surgical procedure. Typically, eye surgical procedures utilize two surgical instruments at a time, thus in an exemplary embodiment, the surgical personnel would typically insert two entry alignment devices into the eye 2.

Figure 7A:
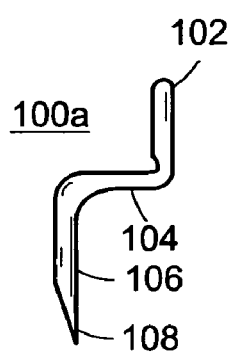
FIGS. 7A,B are front and side views of an entry alignment device according to one embodiment of the present invention.
Figure 7B:
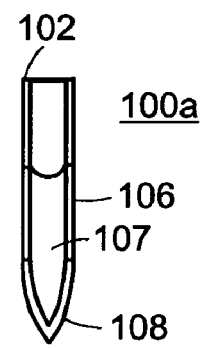

In regards to the illustrated embodiment, and also with reference to FIGS. 7A,B, there is shown an entry alignment device 100a according to one embodiment of the present invention that includes a handle portion 102, a stop portion 104 and an inserted portion 106, that are interconnected to each other so as to form a shoe-horn type of member. It is within the scope of the present invention for any entry alignment device according to the teachings of the present invention, including those specifically described hereinafter, to be used in the sutureless methods according to the present invention.

As illustrated more clearly in FIG. 2, the surgical personnel grasp the handle portion 102 of the entry alignment device 100a with a pair of tweezers 20. The surgical personnel position the entry alignment device 100a such that the pointed end 108 of the inserted portion 106 is at least pointed towards and preferably also is proximal the conjunctiva 4. A force is then applied to the entry alignment device 100a so as to cause the inserted portion pointed end 108 to successively pierce and pass through both of the conjunctiva 4 and the sclera 6. The entry alignment device 100a also is preferably inserted until the stop portion 104 is proximal to the exterior surface of the eye 2. As indicated above, additional entry alignment devices 100a are inserted as required by the needs of the surgical procedure. In the illustrated embodiment, two such entry alignment devices 100a are inserted into the eye.

In an exemplary embodiment, and as more clearly shown in FIG. 2, the inserted portion pointed end 108 is pointed towards the conjunctiva such that a along axis of the inserted portion 106 is orientated so as to be approximately or substantially perpendicular to the exterior surface of the eye at the point of insertion. In this way, the inserted portion pointed end 108 successively pierces and passes through both of the conjunctiva 4 and the sclera 6 generally or substantially perpendicular to each of the conjunctiva and sclera. This is not a limitation, however, as the inserted portion pointed end 108 can be orientated so the long axis is at any angle with respect to the exterior surface of the eye.

Figure 6B:
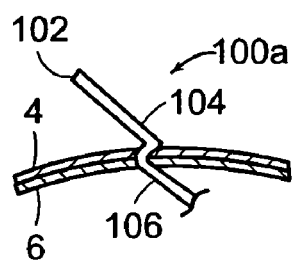
FIG. 6B is an expanded schematic view of a portion of an eye illustrating an alternative method for inserting an entry alignment device into an eye.

Alternatively and as shown in FIG. 6B, the inserted portion pointed end 108 is orientated so that the long axis of the inserted portion is at an angle with respect to the exterior surface or a normal to the exterior surface. In this alternative arrangement, the angle is such that the inserted portion pointed end 108 successively pierces and passes through both of the conjunctiva 4 and the sclera 6 generally along a bias or diagonal with respect to each of the conjunctiva and sclera. With this alternative arrangement, the entrance for the opening formed in the conjunctiva 4 is spaced a distance along the circumference of the eye from the entrance of the opening formed in the sclera 6. Such a configuration allows the conjunctiva 4, which is readily accessible to the surgeon for sealing, to form another mechanism for sealing the sclera 6.

Figure 20A:
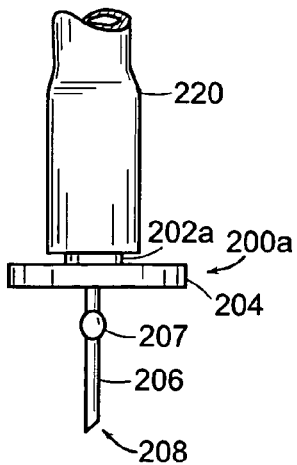
FIG. 20A is a side view of one infusion cannula according to the present invention including a straight through geometry.

In conjunction with, prior to, or following the process of inserting the entry alignment devices, the surgical personnel insert an infusion cannula 200 such as one of the infusion cannulas shown in FIGS. 20A,B, through both of the conjunctiva 4 and sclera 6. This infusion cannula 200 as described below is typically used during the surgical procedure so that fluids can be infused into the intra-ocular volume. As described below in more detail each entry alignment device 100a and the infusion cannula 200 are particularly configured and sized so that their subsequent removal from the conjunctiva 4 and sclera 6 do not involve the use of sutures to seal the openings or apertures that had been formed in the sclera.

After preparing the eye 2 for the insertion of surgical instruments into the intra-ocular volume, the surgical personnel also typically mount a lens assembly (not shown) onto the cornea of the eye in accordance with known and accepted practices and techniques. This lens assembly is provided so that the surgeon can view the interior of the eye as well as any instruments inserted therein.

Figure 17:
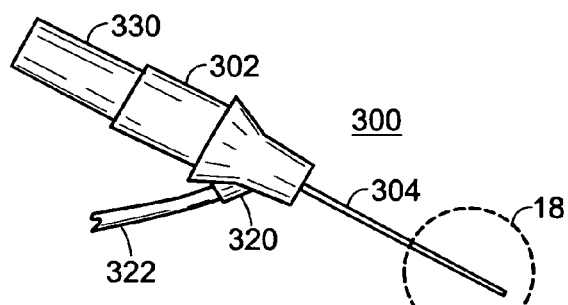
FIG. 17 is a perspective view of a high speed vitreous cutting device according to the present invention.
Figure 18:
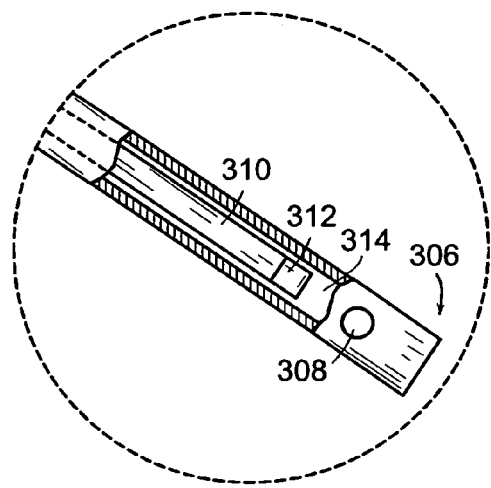
FIG. 18 is an expanded view of the proximal end of the high speed vitreous cutting device illustrated in FIG. 17.

Referring now to FIG. 3, after the eye 2 is so prepared to receive instruments, and in treating a retinal tear or detachment or otherwise treating the posterior segment of the eye, the surgical personnel insert a cutting/aspirating instrument 300, such as that shown in FIGS. 17–18, and a light transmitting instrument 400 through the entry apertures formed by the entry alignment devices 100a and through each of the conjunctiva 4 and the sclera 6. As shown more clearly in FIG. 7B and in FIG. 6A, the inserted portion 106 of the entry alignment device is configured so as to include a dished portion 107 that extends between the stop portion 104 and the pointed end 108. Thus, the curved exterior surfaces of the inserted or operable ends of these instruments 300,400 are received in the dished portion 107 so as to guide each instrument through the conjunctiva 4 and the sclera 6 into the intra-ocular volume as the instrument is being inserted.

The light-transmitting apparatus 400 is configured, as is known in the art, so as to be capable of providing a source of light in the intra-ocular volume. Reference shall be made to the discussion concerning the laser light transmitting source 450 for the structural details of the light transmitting apparatus 400. The cutting/aspirating instrument 300 of the present invention is described in more detail below.

In accordance with known and accepted surgical methods and techniques, the surgical personnel manipulate the light transmitting instrument 400 so the light therefrom is projected within the intra-ocular volume to illuminate the desired area(s). The high speed cutting/aspirating instrument 300 also is disposed in the intra-ocular volume so an end 306 of the inserted member 304, the portion of the instrument that is inserted into the eye, is proximate the retinal tear.

Initially, the vitreous gel, especially all strands causing traction on the retinal tear are removed or aspirated by means of the cutting/aspirating instrument 300. As the vitreous gel is being aspirated, the intraocular volume is maintained by a continuous infusion of a fluid, such as a balanced salt solution (BSS), through the infusion cannula 200. Any subretinal fluid is also aspirated through the retinal tear. As described hereinafter, the cutting/aspirating instrument 300 is preferably configured so as to allow the use of entry alignment devices that can be sized so sutures are not required to seal the opening through the sclera.

Figure 26:
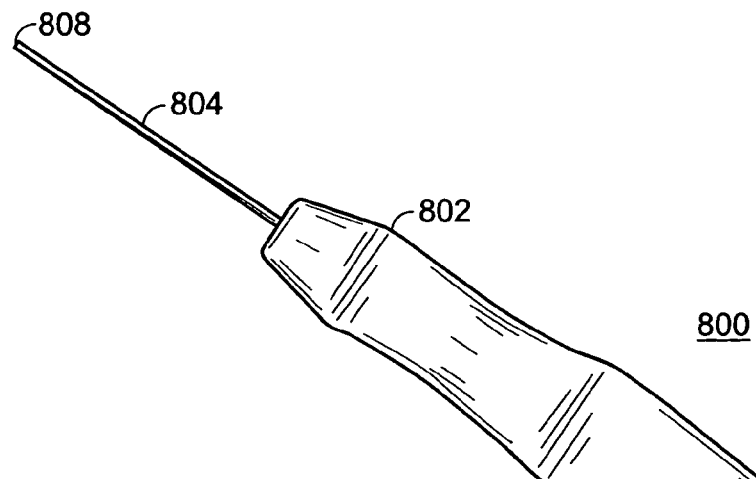
FIG. 26 is a top view of an aspirator according to the present invention.

The vitreous fluid is thereafter aspirated and exchanged with a humidified gas such as air passing through the infusion cannula 200. For example, the cutting/aspiurating instrument is removed from the intra-ocular volume and an aspirator 800, such as that shown in FIG. 26, is inserted through the conjunctiva 4 and the sclera 6 by means of an entry alignment device 100a as hereinabove described. In the method of the present invention, the gas or air being exchanged is preferably humidified by means of a in-line humidifier such as that described in U.S. Pat. No. 5,997,498, the teachings of which are incorporated herein by reference.

Figure 4:
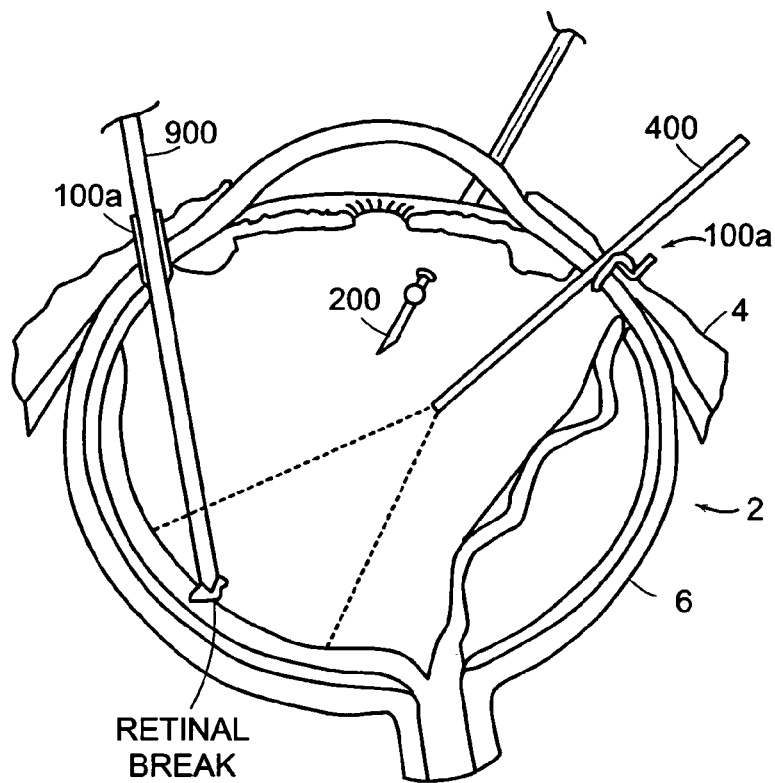
Figure 5:
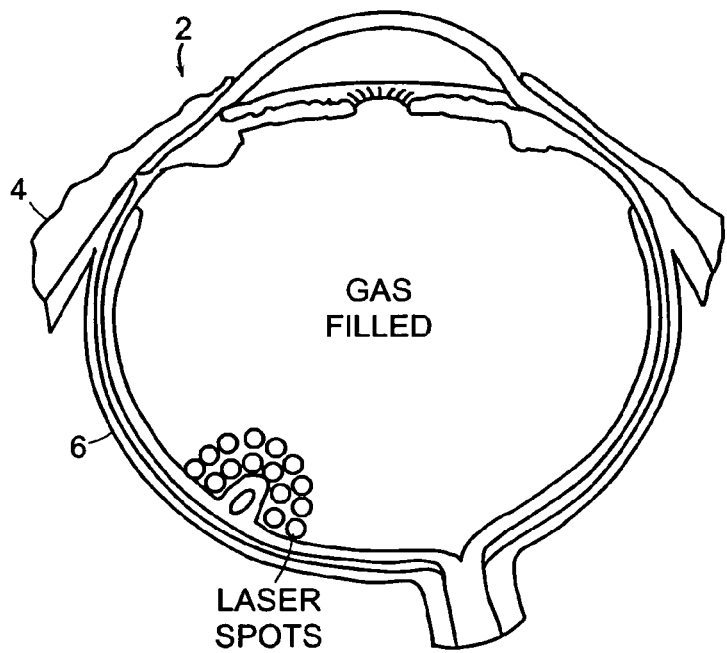

Thereafter, a laser light transmitting instrument 450 (see also FIG. 19) is inserted through each of the conjunctiva 4 and sclera 6 into the intra-ocular volume using an entry alignment device 100a as described hereinabove (see FIG. 4). The retina surrounding the tear is then repeatedly exposed to the laser light from the laser light transmitting instrument 450 so as to form a plurality of heat spots on the retina surrounding the retinal tear (see FIG. 5). In particular, the practitioner manipulates the laser light transmitting instrument 450 so that a plurality of rows of a plurality of such heat spots surrounds the retinal tear. In this way, the retinal tear is photocoagulated with a laser to achieve a thermal adhesive injury. The heat spots also produce scars that prevent fluid from passing through and collecting under the retina. Although the laser photocoagulation technique is illustrated it is within the scope for other techniques known in the art for treating the retinal tear to be used in conjunction with the method of the present invention.

Thereafter, the intra-ocular gas or air, infused while exposing the retina surrounding the retinal tear to laser light, is exchanged for a longer-lasting gas, such as sulfur hexafluorine or perfluoro propane. This longer-lasting gas allows an adequate tamponade time for the therapeutic chorioretinal scar to develop. Preferably, the longer lasting gas being infused also is humidified using an in-line humidifier.

Although the foregoing describes a procedure using the above-identified instruments, this shall not be construed as a limitation on the method of the present invention. It is within the scope of the present invention for other surgical instruments, including for example the below described forceps 600, scissors 700, and directional extendable pick 900, to used or adapted for use with the entry alignment devices and methodology of the present invention.

In the foregoing, a surgical instrument is disposed in an entry aperture thereby preventing or minimizing the potential for leakage of fluid from the intra-ocular volume during the surgical procedure. In the event that one or more instruments are removed from the entry aperture, then the surgical personnel can insert a plug 160 such as that shown in FIG. 28 into the entry aperture to minimize the potential for leakage. This is a particular concern for entry alignment devices that are configured so as to include a lumen that comprises the entry aperture.

More specifically, the surgical personnel grasp the handle portion 162 of the plug 160 with a pair of tweezers 20 for example, orient the plug so the pin or rod portion 164 thereof is pointing towards the entry aperture, and insert the rod portion 164 into the entry aperture. The surgical personnel continue to insert the plug 160 into the entry aperture until the back surface of the flange portion 166 is proximal to the exterior surface of the eye. The reverse would be done to remove the plug 160 from the entry aperture.

After completing the "in eye" portion of the treatment procedure, the inserted instruments, the infusion cannula 200 and each of the entry alignment devices 100a are removed from the eye. As indicated above, the infusion cannula 200 and the entry alignment devices 100a are preferably configured so that the opening in each of the conjunctiva 4 and sclera 6 formed by the infusion cannula or the entry alignment device is self-sealing, that is the openings or holes formed therein do not leak when the infusion cannula or entry alignment device are removed. It is within the scope of the present invention, however, to employ non-suture methods such as hydrogel adhesives, clips and conjunctival sealing to help the entry site of the sclera 6 to seal.

The above-described transconjunctival sutureless viroretinal surgcal procedure, is simpler, safer and faster as compared to prior art surgical methods or procedures. The above-described procedure avoids the dissection of the conjunctiva and its subsequent reattachment to the eye, a requirement of existing prior art surgical methods and techniques. The foregoing procedure, in conjunction with the instruments and devices used in conjunction with this procedure, reduce the size or make smaller the incisions that are made through the sclera for the passage of instruments and infusion cannula, and thus reduce trauma to the eye. Further because there is no need to dissect and reattach the conjunctiva, the time required for the surgical procedure to be performed is reduced, thus also reducing the time the patient is on the operating table and the overall cost of the procedure.

As indicated above, in the methods according to the present invention there is provided one or more entry alignment device. Each of these entry alignment devices is configured and arranged so it successively pierces and passes through the conjunctiva 4 and the sclera 6 and so it maintains the alignment of the openings or apertures made in each of the conjunctiva and sclera, thereby forming an entry aperture in the eye that extends between the exterior surface of the eye and the intra-ocular volume. As also indicated above, such entry alignment devices are preferably configured and sized so the opening or aperture in the sclera 6 made by the device is sealable without the use of sutures. There is shown in FIGS. 7–12 various embodiments of entry alignment devices according to the present invention. It should be recognized from the outset that the devices shown in each of FIGS. 7–12 are exemplary and not exhaustive of all possible entry alignment device configurations or designs that can be used in the methods according to the present invention. Reference also should be made to FIGS. 1–6 for any elements of features not specifically shown or specifically described hereinafter in any of FIGS. 7–12.

Referring now to FIGS. 7A,B, there is shown one embodiment of an entry alignment device 100a according to the present invention. As described above, such an entry alignment device 100a includes a handle portion 102, a stop portion 104, and an inserted portion 106 having a pointed end 108 and a dished portion 107. In addition to that described above, the inserted portion 106 is sized so as to have a width that is sufficiently small such that the removal of the inserted portion from the sclera 6 leaves an incision or opening that does not require sutures to seal the opening or incision. In an exemplary embodiment, the width of the inserted portion is about 0.020 inches. The stop portion 104 has a width and length sufficient to prevent the entry alignment member 100a from being drawn into the intra-ocular volume during the surgical procedure.

The dished portion 107 is configured geometrically to complement the geometric shape of the surgical instruments that can be inserted into the eye 2. In the exemplary illustrated embodiments for the surgical instruments herein described, the inserted portion thereof is generally of a cylindrical shape and thus the dished portion 107 is generally configured so as to be generally arcuate.

The pointed tip 108 of the inserted portion is generally configured so as to form a non-traumatic tip that minimizes damage to the tissue comprising the conjunctiva 4 and the sclera 6 as well as structures within the eye 2. In an exemplary embodiment, the pointed tip 108 is tri-beveled and sharpened like a needle to facilitate insertion.

The shoe-horn embodiment of the entry alignment device 100a is made from any material known in the art which has sufficient rigidity and strength to be inserted into and removed from the conjunctiva 4 and sclera 6 as described above and to withstand in use stresses arising for example from the insertion and/or manipulation of surgical instruments as well motion of the eye or elements thereof. Also, the material shall be inclusive of materials capable of being used with the desired sterility required for the surgical procedure. In exemplary embodiments, this entry alignment device is made from metals such as stainless steel and plastics such as polyimide.

Figure 8:
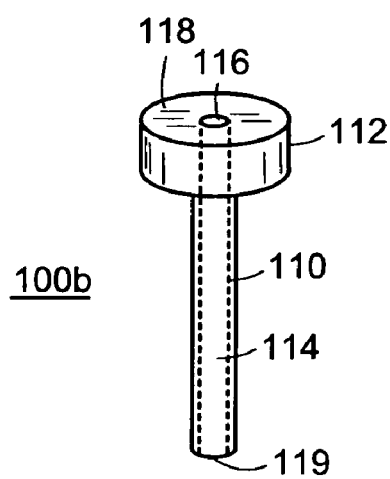
FIG. 8 is a perspective view of an entry alignment device according to a second embodiment of the present invention.

Now referring to FIG. 8 there is shown a second embodiment of an entry alignment device 100b according to the present invention that includes an insertion member 110 and a stop member 112 that is affixed about the exterior of the insertion member 110. The entry alignment device 100b of this embodiment is configured and arranged so that in use, the portion of the insertion member 110 that is below the stop member 112 is passed through each of the conjunctiva 4 and the sclera 6. Additionally, in use the entry alignment member 100b is inserted until the stop member 112 is proximal the exterior surface of the eye 2 similar to that shown for the stop portion 104 in FIG. 6A.

In the illustrated embodiment, an end of the insertion member 110 is securably received in the stop member 112. Alternatively, the entry alignment device is constructed such that the insertion and stop members 110,112 form an integral structure. In yet another embodiment, the insertion member 110 and stop member 112 are configured and arranged so the insertion member extends through an aperture in the stop member. In this case an end of the insertion member is disposed proximal an end surface 118 of the stop member or the insertion member extends outwardly from the stop portion end surface. The insertion member 110 also is a tubular member having a lumen 114 extending between the ends of the insertion member and the stop portion includes therein a through aperture 116 that communicates with the insertion member lumen. In use, the lumen 114 and the through aperture 116 comprises the entry aperture formed in the eye 2 through which the surgical instruments are inserted.

The insertion member lumen 114 and stop portion through aperture 116 are sized and arranged so as to be capable of slidably receiving therein the insertable portions of the surgical instruments. In particular, they are configured so as to complement the geometric arrangement of these insertable portions. In an exemplary embodiment, the diameter of the lumen 114 and the through aperture 116 are established so as to be capable of receiving therein surgical instruments insertable portions having a cross-sectional diameter of about 25 gauge. The insertion member 110 also is configured and sized so that the outer diameter or cross-section thereof is sufficiently small such that the removal of the inserted member from the sclera 6 leaves an incision or opening therein that does not require sutures to seal the opening or incision. It is within the scope of the present invention for the insertion member 110 to have any outside geometric configuration, including oval and hexagonal, that is otherwise consistent with the teachings of the present invention, specifically that entry alignment device 100b removal leaves an opening in the sclera that need not be closed by sutures, more preferably an opening that is self-sealing.

The inserted end 119 of the insertion member 110 is illustrated as being substantially flat. It is within the scope of the present invention, however, for the inserted end 119 to be pointed, cut on a bias or other wise configured so as to form a tissue piercing type of end.

The stop member 112 is configured and arranged so as to provide a sufficient surface area and thickness to prevent the entry alignment member 100b from being drawn into the intra-ocular volume. The stop member 112 also is sized so as to provide a sufficiently large surface area for the surgical personnel to be able to identify and locate the entry alignment device 100b on the exterior surface of the eye. The stop member 112 also is configured so as to provide a mechanism by which the surgical personnel can grasp the entry alignment device 100b when it is to be removed from and/or inserted into the eye. In an exemplary embodiment, this grasping mechanism comprises a groove in the vertical surfaces of the stop member 112 or a surface artifact or protrusion on the stop member.

The insertion member 110 and stop member 112 are made from any material known in the art that has sufficient rigidity and strength to be inserted into and removed from the conjunctiva 4 and sclera 6 as described above and to withstand in use stresses arising for example from the insertion and/or manipulation of surgical instruments as well motion of the eye or elements thereof. Also, the material shall be inclusive of those materials that are capable of being used with the desired sterility required for the surgical procedure. The materials also should be such that the stop member 112 can be secured or affixed to the insertion member 110. More particularly, the insertion member 110 and stop member 112 are made from metals such as stainless steel and plastics such as polyimide or combinations thereof.

In an exemplary preferred embodiment, the insertion member is made from polyimide and has an outer diameter of about 23–24 gauge (about 0.025–0.022 inches). Such an outer diameter is particularly advantageous because the incision or opening in the sclera is generally self-sealing.

Figure 9:
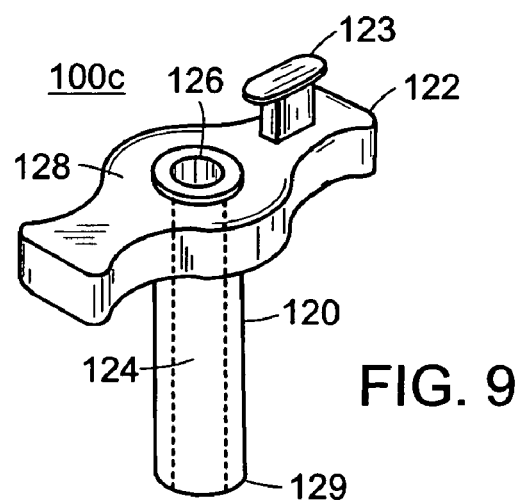
FIG. 9 is a perspective view of an entry alignment device according to a third embodiment of the present invention.

Now referring to FIG. 9 there is shown an entry alignment device 100c according to a third embodiment, in the shape of a conventional cannula, that includes an insertion member 120 and a stop member 122 that is affixed to the insertion member. In a particular embodiment, the insertion member and the stop member form an integral, one-piece structure. The entry alignment device 100c of this embodiment is configured and arranged so that in use the portion of the insertion member 120 that is below the stop member 122 is passed through each of the conjunctiva 4 and the sclera 6. Additionally, in use the entry alignment member 100b is inserted until the stop member 122 is proximal the exterior surface of the eye 2 similar to that shown for the stop portion 104 in FIG. 6A.

In the illustrated embodiment, the insertion member 120 is a tubular member having a lumen 124 extending between the ends of the insertion member and the stop member 122 includes therein a through aperture 126 that communicates with the insertion member lumen. In use, the lumen 114 and the through aperture 116 comprise the entry aperture formed in the eye 2 through which the surgical instruments are inserted.

The insertion member lumen 124 and stop member through aperture 126 are sized and arranged so as to be capable of slidably receiving therein the insertable portions of the surgical instruments. In particular, they are configured so as to complement the geometric arrangement of these insertable portions. In an exemplary embodiment, the diameter of the lumen 124 and the through aperture 126 are established so as to be capable of receiving therein surgical instruments insertable portions having a cross-sectional diameter of about 25 gauge. The insertion member 120 also is configured and sized so that the outer diameter or cross-section thereof is sufficiently small such that the removal of the inserted member from the sclera 6 leaves an incision or opening therein that does not require sutures to seal the opening or incision. It is within the scope of the present invention for the insertion member 120 to have any outside geometric configuration, including oval and hexagonal, that is otherwise consistent with the teachings of the present invention, specifically that entry alignment device 100c removal leaves an opening in the sclera that need not be closed by sutures, more preferably an opening that is self-sealing.

The inserted end 129 of the insertion member 120 is illustrated as being substantially flat. It is within the scope of the present invention, however, for the inserted end 129 to be pointed and cut on a bias or other wise configured so as to form a tissue piercing type of end.

The stop member 122 is configured and arranged so as to provide a sufficient surface area and thickness to prevent the entry alignment member 100c from being drawn into the intra-ocular volume. The stop member 122 also is sized so as to provide a sufficiently large surface area for the surgical personnel to be able to identify and locate the entry alignment device 100c on the exterior surface of the eye. The stop member 122 also includes a surface artifact 123 that is configured so as to provide a mechanism by which the surgical personnel can grasp the entry alignment device 100c for insertion into and removal from the eye. In an exemplary embodiment, this grasping mechanism is used in conjunction with an insertion tool, such as that shown in FIGS. 13–15 for insertion and/or removal of the device.

The insertion member 120 and stop member 122 are made from any material known in the art that has sufficient rigidity and strength to be inserted into and removed from the conjunctiva 4 and sclera 6 as described above and to withstand in use stresses arising for example from the insertion and/or manipulation of surgical instruments as well motion of the eye or elements thereof. Also, the material shall be inclusive of those materials that are capable of being used with the desired sterility required for the surgical procedure. More particularly, the insertion member 110 and stop member 112 are made from metals such as stainless steel and plastics such as polyimide or combinations thereof.

In an exemplary embodiment, the insertion member is made from stainless steel has an outer diameter of about 22–23 gauge (about 0.028–0.025 inches).

Figure 10A:
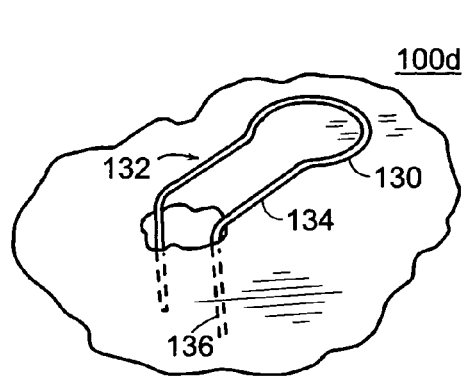
FIG. 10A is a perspective view of an entry alignment device according to a fourth embodiment of the present invention when inserted into the eye.

Now referring to FIGS. 10A,B there is shown entry alignment devices 100d,e according to a fourth embodiment of the present invention that are formed by shaping a solid or hollow cylindrical member, for example a metal wire, into a predetermined shape or configuration. In FIG. 10A there is shown an entry alignment device 100d including an arcuate portion 130 from which extends two leg portions 132 that are spaced from each other and generally parallel to each other. Each leg portion includes an upper segment 134 and a lower segment 136, where the lower segment is at an angle with respect to the upper segment so that the upper segment.

The lower segments 136 are sized so that each extends through the conjunctiva 4 and sclera 6 when disposed in the entry aperture. The angle between the upper segments 134 and the lower segments 136 is established and the upper segments are sized so that the upper segments act as a stop, to limit the amount of insertion as well as to restrain the entry alignment device 100d from drifting into the intra-ocular volume during the surgical procedure.

In one specific embodiment, the surgical personnel form an entry aperture having the desired size in the conjunctiva 4 and the sclera using for example by means of a stylet. Thereafter, the surgical personnel insert the leg portion lower segments 136 into the entry aperture about the stylet and following insertion of the lower segments 136 the stylet is removed from the eye. In another specific embodiment, the leg portion lower segments 136 are secured to an insertion device and the portion of the insertion device containing the lower segments 136 is inserted into the eye so as to form the entry aperture in the conjunctiva 4 and the sclera 6. Thereafter, the insertion tool is removed leaving the lower segments 136 in the entry aperture.

The spring resiliency of the leg portions 132 and the arcuate portion 130 act so as to keep the lower segments 136 spaced from each other when they are disposed in the entry aperture. Consequently, this spring resiliency and the lower segments 136 maintain the entry aperture in the eye and thus also maintains the alignment of the portions of the entry aperture in the conjunctiva 4 and the sclera 6. The leg portion upper segments 134 also comprise a mechanism for limiting the motion of the entry alignment device 100*d* into the eye (e.g., act as a stop).

Figure 10B:
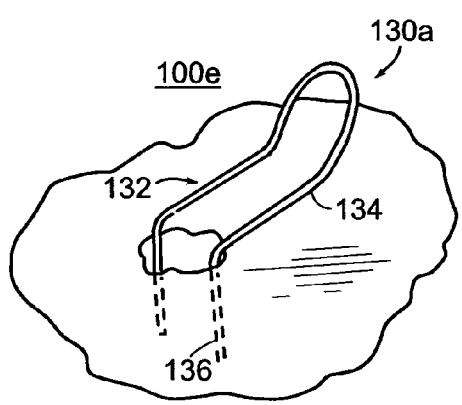
FIG. 10B is a perspective view of an alternative embodiment of the entry alignment device of FIG. 10A.

There is shown in FIG. 10B an alternative entry alignment device 100*e* that is similar in most respects to the entry alignment device of FIG. 10A except that in the alternative embodiment, the arcuate portion 130*a* is arranged so as to be at an angle with respect to the leg portions 132 to facilitate the removal of the entry alignment device 100*e* from the eye upon completion of the surgical procedure. Accordingly, reference shall be made to the foregoing discussion for FIG. 10A for other details of the alternative entry alignment device 100*e*.

In an exemplary preferred embodiment, the entry aperture being formed is sized so as to be capable of receiving therein surgical instruments insertable portions having a cross-sectional diameter of about 25 gauge. The leg portion lower segments 136 also are preferably spaced from each other so as to maintain two opposing interior surfaces of the entry aperture spaced from each other so as to meet this capability.

The entry alignment devices 100*d,e* are made from any of a number of materials known in the art which have sufficient strength and the desired spring characteristics when in the illustrated shapes to function in the manner described above. Such materials includes metals such as stainless steel and plastics.

Figure 11:
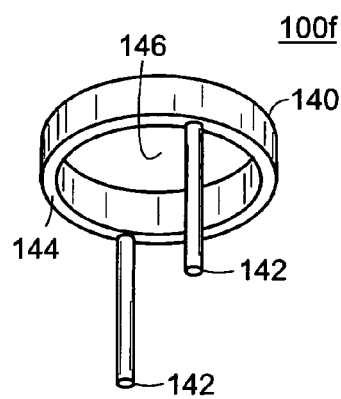
FIG. 11 is a perspective view of an entry alignment device according to fifth embodiment of the present invention.

There is shown In FIG. 11 an entry alignment device 100*f* according to a fifth embodiment of the present invention that includes a stop member 140 and two or more displacing members 142 that are secured to the stop member. The displacing members 142 also extend outwardly, downwardly in the illustrated embodiment, from a back surface 144 of the stop member 140.

The displacing members 142 are sized so that each extends through the conjunctiva 4 and sclera 6 when disposed in an entry aperture. As with the other above-described entry alignment devices 100*a–e*, the stop member 140 is configured and sized so as to limit the amount of insertion, and to restrain the entry alignment device 100*f* from drifting into the intra-ocular volume during the surgical procedure as well as to provide a target for the surgical personnel during the procedure. The two or more displacing members are displaced from each other such that when the displacing members are inserted into the entry aperture at least two opposing interior surfaces of the entry aperture are maintained spaced from each other so that surgical instruments can be inserted into the entry aperture. The stop member 140 also is configured with an aperture 146 that is sized so the surgical instruments can be passed there through.

Figure 16:
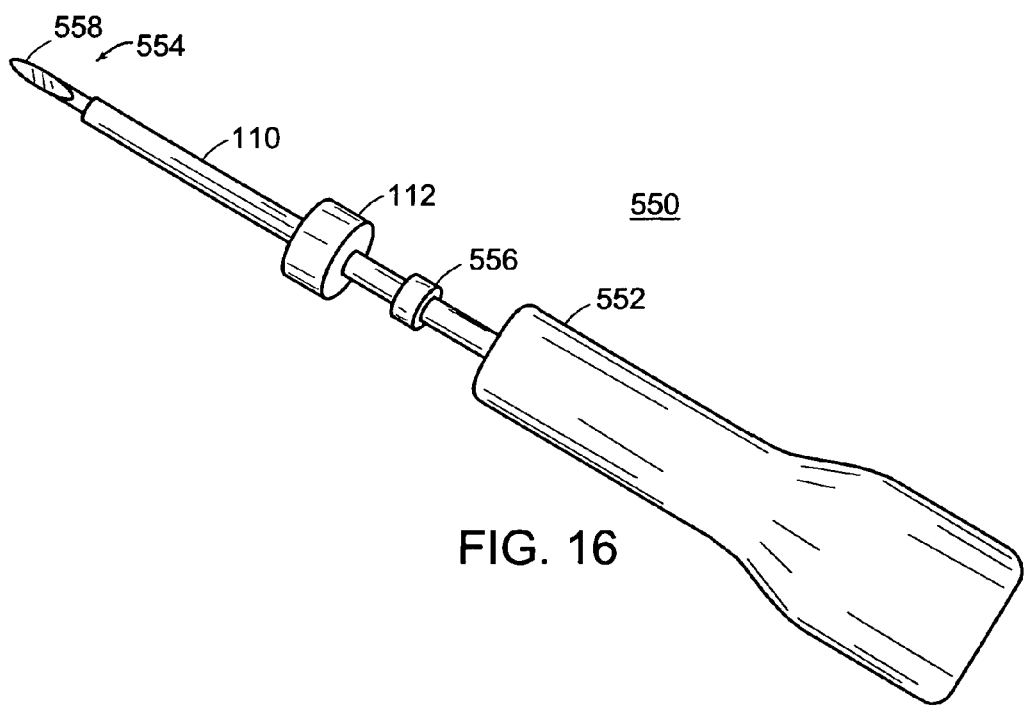
FIG. 16 is a perspective view of another exemplary insertion tool for inserting an entry alignment device according to the present invention.

In use, the surgical personnel mount the entry alignment device on an insertion tool, for example, the insertion tool shown in FIG. 16 so that the displacing members are disposed on either side of the stylet having the generally desired size for an entry aperture. The stylet is inserted into the eye until the stop member back surface 144 is proximal the exterior surface of the eye, thereby forming the entry aperture in the conjunctiva 4 and the sclera 6. At the same time, the displacing members 142 are inserted into the so formed entry aperture so that each extends through each of the conjunctiva 4 and the sclera 6. The stylet is then removed leaving the displacing members 142 in the entry aperture In an exemplary preferred embodiment, the entry aperture being formed is sized so as to be capable of receiving therein surgical instruments insertable portions having a cross-sectional diameter of about 25 gauge. The displacing members also are preferably spaced from each other so as to maintain at least two opposing interior surfaces of the entry aperture spaced from each other so as to meet this capability. The stop member through aperture 146 also is sized so as to be capable of receiving therein surgical instruments insertable portions having a cross-sectional diameter of about 25 gauge.

The entry alignment devices 100*f*, including the stop member 140 and the displacing members 142, are made from any of a number of materials known in the art which have sufficient rigidity and strength to be inserted into and removed from the conjunctiva 4 and sclera 6 as described above and to withstand in use stresses arising for example from the insertion and/or manipulation of surgical instruments as well motion of the eye or elements thereof. Also, the material shall be inclusive of those materials that are capable of being used with the desired sterility required for the surgical procedure. Such materials includes metals such as stainless steel and plastics, such as polyimide.

Figure 12:
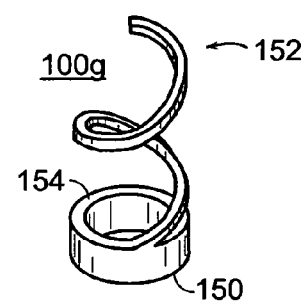
FIG. 12 is a perspective view of an entry alignment device according to sixth embodiment of the present invention.

There is shown in FIG. 12 an entry alignment device 100*g* according to a sixth embodiment of the present invention that includes a stop member 150 and a helical member 152 that is secured to the stop member. The helical member 152 also extends outwardly from a back surface 154 of the stop member 150.

The helical member 152 is sized so that it has an axial length sufficient to extend through the conjunctiva 4 and sclera 6 and into the intra-ocular volume when disposed in an entry aperture. The helical member 152 also is sized such that the inner diameter of the helix is large enough for the insertable portions of the surgical instruments to pass there through. As with the other above-described entry alignment devices 100*a–f*, the stop member 150 is configured and sized so as to limit the amount of insertion and to restrain the entry alignment device 100*g* from drifting into the intra-ocular volume during the surgical procedure as well as to provide a target for the surgical personnel during the procedure. The stop member also is configured with an aperture 156 that is sized so the insertable portions of the surgical instruments can be passed there through.

In use, the surgical personnel insert the helical member 152 into the eye and twist the entry alignment device 100*g* in the appropriate direction so as to in effect screw the entry alignment member into the eye. The surgical personnel continue to twist the entry alignment member 100*g* until the back surface 154 thereof is proximal the exterior surface. In this condition, the helical member 152 extends through each of the conjunctiva 4 and the sclera 6 into the intra-ocular volume. To remove the entry alignment device 100*g* the surgical personnel twist the device in an opposite direction, thereby unscrewing the device from the eye.

In an exemplary preferred embodiment, the entry aperture being formed is sized so as to be capable of receiving therein surgical instruments insertable portions having a cross-sectional diameter of about 25 gauge. The inner diameter of the helix as well as the stop member through aperture 156 also are sized so as to be capable of receiving therein surgical instruments insertable portions having a cross-sectional diameter of about 25 gauge.

The entry alignment devices 100*g*, including the stop member 150 and the helical member 152, is made from any of a number of materials known in the art which have sufficient rigidity and strength to be inserted into and removed from the conjunctiva 4 and sclera 6 as described above and to withstand in use stresses arising for example from the insertion and/or manipulation of surgical instruments as well motion of the eye or elements thereof. Also, the material shall be inclusive of those materials that are capable of being used with the desired sterility required for the surgical procedure. Such materials includes metals such as stainless steel and plastics, such as polyimide.

Figure 13:
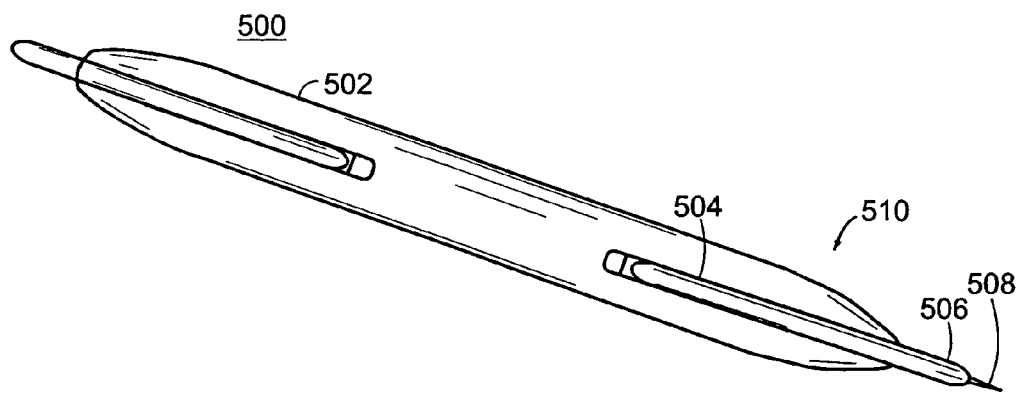
FIGS. 13–15 are various views of an exemplary insertion tool for inserting an entry alignment device according to the present invention into an eye.
Figure 14:
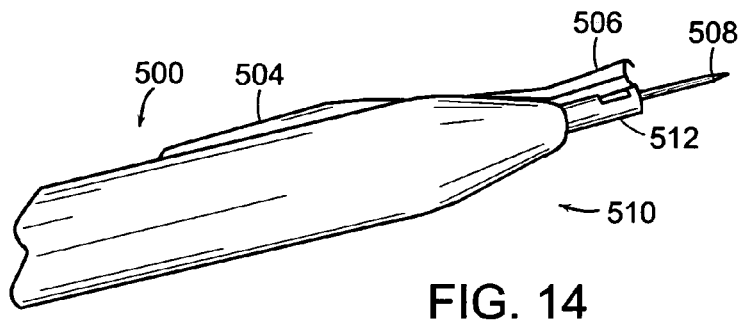
Figure 15:
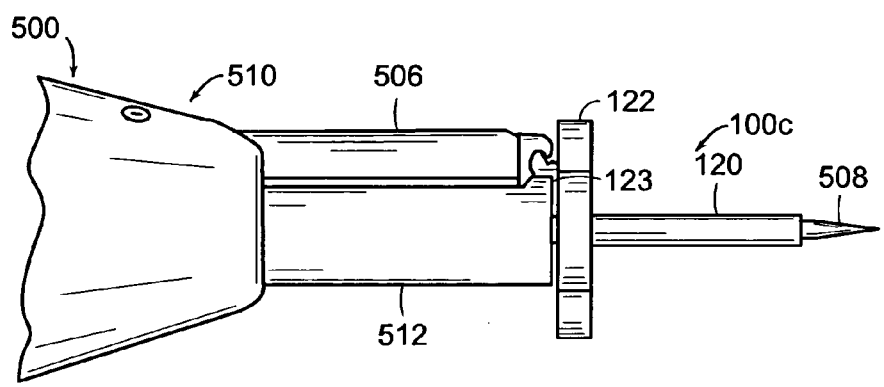

Referring now to FIGS. 13–15, there are shown various views of one exemplary entry alignment device insertion tool 500 according to the present invention. Such an insertion tool 500 includes a handle member 502, a moveable member 504 being moveably disposed with the handle member and a fixed stylet 508 projecting outwardly from one end 510 of the handle member. The handle member 502 is generally configured so as to provide a shape that is readily grasped by the surgical personnel.

The moveable member 504 includes a device grasping portion 506 and is pivotably disposed within the handle member 502 so that the device grasping portion 506 can be selectively moved between a grasping position and a mounting position. In the mounting position, as more clearly shown in FIG. 14, the moveable member 504 is depressed into the handle member 504 so as to cause the device grasping portion 506 to move away from the stylet 508 thus preparing the insertion tool 500 so an entry alignment device can be mounted thereon. Thereafter the movable member 504 is released thereby preferably causing the device grasping portion to move towards the stylet 508 thereby grasping the device and removably securing the entry alignment device to the insertion tool 500 as more clearly shown in FIG. 15.

For example, and also with reference to FIG. 9, the stylet 508 is slid into the lumen 124 of the entry alignment device 100c until the enlarged portion 512 of the stylet rests against the top surface of the stop member 122. Additionally, the entry alignment device is arranged so the stop member surface artifact 123 is proximal the side of the stylet enlarged portion 512 where the device grasping portion 506 is positioned. When the entry alignment device 100c is thus disposed on the stylet 508, the moveable member 504 is released so the device grasping portion 506 is moved into the grasping position. In the grasping position, and as shown more clearly in FIG. 15, the grasping portion envelops a part of the surface artifact 123 so as to secure the entry alignment device 100c to the insertion tool 500.

In use, the surgical personnel position the pointed end of the stylet 508 at the desired location for an entry aperture or access port and insert the stylet pointed end into the eye so as to successively pierce and pass through the conjunctiva 4 and the sclera 6 and so as to simultaneously insert the device inserted member 120 therein. The pointed end of the stylet 508 is preferably beveled and sharpened like a needle to facilitate insertion of the stylet into and through the conjunctiva 4 and the sclera 6. Insertion is stopped when the back surface of the stop member 122 is resting upon the exterior surface of the eye. The movable member 504 is again depressed so the device grasping portion 506 moves away from the entry alignment device 100c thereby freeing the device. The surgical personnel, while maintaining the movable member depressed withdraw the stylet 508 from the device lumen 124, thus leaving the entry alignment device 100c disposed in the eye.

Referring now to FIG. 16, there is shown another exemplary entry alignment device insertion tool 550 according to the present invention. Such an insertion tool 500 includes a handle member 552 and a stylet 554 affixed to and extending outwardly from an end of the handle member. The handle member 552 is generally configured so as to provide a shape that is readily grasped by the surgical personnel.

The stylet 554 is a generally cylindrical member being sized so as to be capable of being received in the lumen of an entry alignment device. The stylet includes a stop 556 that is generally in the form of an enlarged region of the cylindrical member area to restrain motion of the entry alignment device along the length of the stylet. The end 558 of the stylet 554 opposite the handle member 552 is preferably beveled (e.g., tri-leveled) and sharpened like a needle to facilitate insertion of the stylet into and through the conjunctiva 4 and the sclera 6.

For example, and with reference to FIG. 8, the surgical personnel slid the stylet 554 through the lumen 114 of the entry alignment device 100b until the top surface of the stop member 112 rests against the stylet stop 556. In use, the surgical personnel position the stylet pointed end 558 at the desired location for an entry aperture or access port and insert the pointed end into the eye so as to successively pierce and pass through the conjunctiva 4 and the sclera 6 and so as to simultaneously insert the device insertion member 110 therein. Insertion is stopped when the back surface of the stop member 112 is resting upon the exterior surface of the eye. The surgical personnel, then withdraw the stylet 554 from the device lumen 114, thus leaving the entry alignment device 100b disposed in the eye.

Referring now to FIGS. 17–18 there is shown a high-speed vitreous cutting and aspirating device 300 according to the present invention that includes an interface member 302, an inserted member 304 having a lumen 314 and a side aperture 308 proximal to an end thereof. The cutting and aspirating device 300 further includes a moveable member 310, having a guillotine end 312 for cutting, that is disposed within the lumen 314 and operably and mechanically connect to the interface member 302.

An end of the interface member 302 is secured to a cutter head 330 such as the Lightning Cutter manufactured by Bausch and Lomb, which cutter head is operably and mechanically connected to the moveable member 310 via the interface member 302 so that the moveable member moves cyclically back and forth within the lumen 314 responsive to the cutter head. More specifically, the moveable member guillotine end 312 is moved back and forth across the side aperture 308 proximal the end 306 of the inserted member 304, whereby material disposed in the side aperture is successively cut by the guillotine end 312. The interface member 302 includes a suction port 320 that is connected to a suction source (not shown) by a suction line 322. The suction port 320 is in fluid communication with the lumen 314 so that fluid and cut material is drawn up through the lumen about the movable member 310 and out the suction port.

The inserted member 304 is configured and sized so as to be useable with an entry alignment device of the present invention. More particularly, the inserted member 304 also is configured and sized so the outer diameter or cross-section thereof is sufficiently small such that the removal of the inserted member from the sclera 6 leaves an incision or opening therein that does not require sutures to seal the opening or incision. In an exemplary embodiment, the outer diameter or cross-section of the inserted member 304 is about 25 gauge.

The moveable member 310 is moved cyclically by the cutter head 330 so that the cut vitreous material can be continuously aspirated from the lumen 314 without clogging thereof. In preferred embodiments, the moveable member 310 is operated such that the guillotine end 312 makes about 1000 cuts per minute (cpm), more preferably at least 1000 cpm and in a more specific embodiment is operated in the range of from about 1000 to 1500 cpm. Such cut rates have been found to be particularly advantageous because vitreous material being cut by the guillotine end 312 is successfully and continuously aspirated out of the suction port 320 without clogging of the lumen 314 of an inserted member 304 having an outer diameter of 25 gauge. Tests also have shown that there is clogging of the lumen for a cutting and aspirating device having an inserted member outer diameter of about 25 gauge when using prior art pneumatic cutter heads to drive the moveable member.

Additionally, the suction pressure developed at the suction source or suction port 320 is sufficient to readily draw the cut material and any fluid up through the lumen and out of the suction port. In an exemplary embodiment, the suction pressure is about 400 mmHg and more particularly the suction pressure is 400 mmHG or greater.

Figure 19:
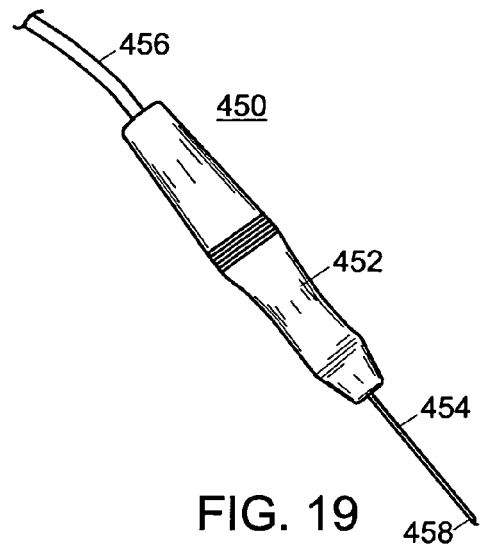
FIG. 19 is a perspective view of a laser light transmitting source.

Referring now to FIG. 19, there is shown a perspective view of a laser light transmitting source 450 according to the present invention that includes a handle portion 452, a insertable member 454 and an optical cable 456. The handle member 452 is generally configured so as to provide a shape that is readily grasped by the surgical personnel.

The optical cable 456 is any of a number of optical cables known in the art that can communicate light between the ends of the cable. The optical cable 456 also includes the optical couplers that optically couple the cable to another component such as a light source. One end of the optical cable 456 is optically coupled to a light source (not shown) and the other end of the optical cable is optically coupled to the insertable member 454. The insertable member 454 is configured so as to include a lumen that forms a passage for the light coming from the optical cable 456. In this way, the light being generated by the light source is projected from the open end 458 of the insertable member 454 onto the desired area of the eye as hereinabove described.

The insertable member 454 is configured and sized so as to be useable with an entry alignment device of the present invention. More particularly, the insertable member 454 also is configured and sized so the outer diameter or cross-section thereof is sufficiently small such that the removal of the insertable member from the sclera 6 leaves an incision or opening therein that does not require sutures to seal the opening or incision. In an exemplary embodiment, the outer diameter or cross-section of the insertable member 454 is about 25 gauge.

Now referring to FIGS. 20A,B there is shown two exemplary infusion cannulas 200*a,b* according to the present invention. Referring to FIG. 20A, the infusion cannula 200*a* includes a nozzle portion 202*a*, a stop portion 204 and a inserted portion 206. The nozzle portion 202*a* is a generally cylindrical hollow member that extends outwardly from the stop portion 204. The nozzle portion 202*a* is configured so as to receive thereabout an inlet line 220 that is interconnected to an infusion source, for example an elevated bottle of balanced saline solution or a source of pressurized gas such as air.

The stop portion 204 is configured and arranged so as to provide a sufficient surface area and thickness to prevent the infusion cannula 200*a* from being drawn or drifting into the intra-ocular volume of the eye. The stop portion 204 and the inserted portion 206 are configured so as to include in each a lumen that communicates with each other and the lumen in the nozzle portion 202*a*. In this way, the fluid from the infusion source flows through the successive lumens and into the intra-ocular volume of the eye.

The insertable portion 206 is configured and sized so the outer diameter or cross-section thereof is sufficiently small such that the removal of the insertable portion from the sclera 6 leaves an incision or opening therein that does not require sutures to seal the opening or incision. In an exemplary embodiment, the outer diameter or cross-section of the insertable portion 206 is about 25 gauge. In more particular embodiments, the inserted end 208 of the insertable portion 206 is beveled, preferably tri-beveled, and sharpened like a needle so as to minimize trauma and damage to the tissues of eye, as the inserted end pierces and passes through the conjunctiva 4 and the sclera 6 into the intra-ocular volume. The insertable portion 206 is configured with a retaining ball 207 or other surface artifact that helps to constrain the cannula 200*a* within the sclera 6.

Figure 20B:
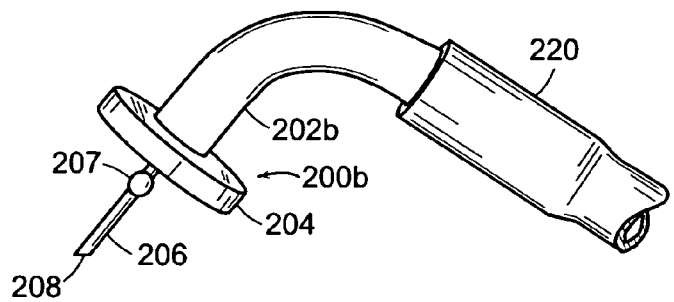
FIG. 20B is a perspective view of another infusion cannula according to the present invention including an at-an-angle geometry.

There is shown in FIG. 20B another infusion cannula 200*b* according to the present invention that includes a nozzle portion 202*b*, a stop portion 204 and an insertable portion 206. The nozzle portion 200*b* of this embodiment differs from that described for the other infusion cannula embodiment illustrated in FIG. 20A in that a portion of the nozzle portion 204 is arcuate so the inlet line connection of the nozzle portion is at an angle with respect to the lumen of the insertable portion. In the illustrated embodiment, the inlet line connection is at 90 degrees angle, however other angles are contemplated for use in the present invention. Reference shall be made to the foregoing discussion for the other infusion cannula embodiment illustrated in FIG. 20A for other details or features.

Now referring to FIGS. 21–23 there are shown various views of a forceps 600 according to the present invention, that includes a handle member 610 and a head 630, a portion of which is configurable for insertion into the intra-ocular volume. The handle member 610 is generally configured so as to provide a shape that is readily grasped by the surgical personnel and so as to include one or more actuation members 612. The handle member 610 is further configured such when the actuation members 612 are moved in one direction an axial movement or force is generated by the handle member in one direction and when the actuation members are moved in another direction an axial movement or force is generated by the handle member in opposite direction. In an exemplary embodiment, the product sold under than name of ErgoTec by Bausch and Lomb comprises the handle member 610 according to the present invention.

The head 630 includes a mechanical interconnecting portion 632, an insertable portion 634 having a lumen 636 and a sloped end 638, and a moveable member 640 having a sloped end 642 that is disposed in the lumen. As shown in phantom in FIG. 23, the sloped end 638 preferably is formed by machining away all but a small segment of the insertable portion and bending this small segment upwardly to form the sloped end.

The mechanical interconnecting portion 632 is affixed to the handle member 610 so the head 630 extends from an end thereof. The mechanical interconnecting portion 632 also is mechanically interconnected to the handle member 610 and the moveable member 640 such that the moveable member moves back and forth axially in the lumen 636 responsive to the axial movement or force generated by the actuation members 612 of the handle member 610. In this way, when the actuation members 612 are in a rest position, the movable member sloped end 642 is remote from the insertable portion sloped end 638, leaving a space therebetween. Correspondingly, when the actuation members 612 are actuated, the moveable member sloped end 642 is moved towards the insertable portion sloped end 638 thereby reducing the space therebetween or putting the sloped ends into contact with each other. Preferably, the sloped ends 638, 642 of each of the insertable portion 634 and the moveable member 640 are configured so the sloped end surfaces are essentially parallel to each other. In other words, the opposing surfaces of the sloped ends 638,642 provide a mechanism by which material can be grasped by the surgical personnel responsive to the movement of the actuation members 612.

In use, the surgical personnel insert the insertable portion 634 into the entry aperture so the sloped end 638 thereof is dispose in the intra-ocular volume of the eye. Thereafter, the surgical personnel manipulate the forceps so some loose material such as free strand of vitreous gel is disposed in the sloped end 638. The surgical personnel then actuate the actuation members 612 causing the moveable member 640 to moved axially within the lumen towards the insertable portion sloped end 638, to trap the loose material between the opposing faces of the insertable portion sloped end and the moveable member sloped end 642.

The insertable portion 634 is configured and sized so as to be useable with an entry alignment device of the present invention. More particularly, the insertable portion 634 also is configured and sized so the outer diameter or cross-section thereof is sufficiently small such that the removal of the insertable portion from the sclera 6 leaves an incision or opening therein that does not require sutures to seal the opening or incision. In an exemplary embodiment, the outer diameter or cross-section of the insertable portion 634 is about 25 gauge.

Figure 25:
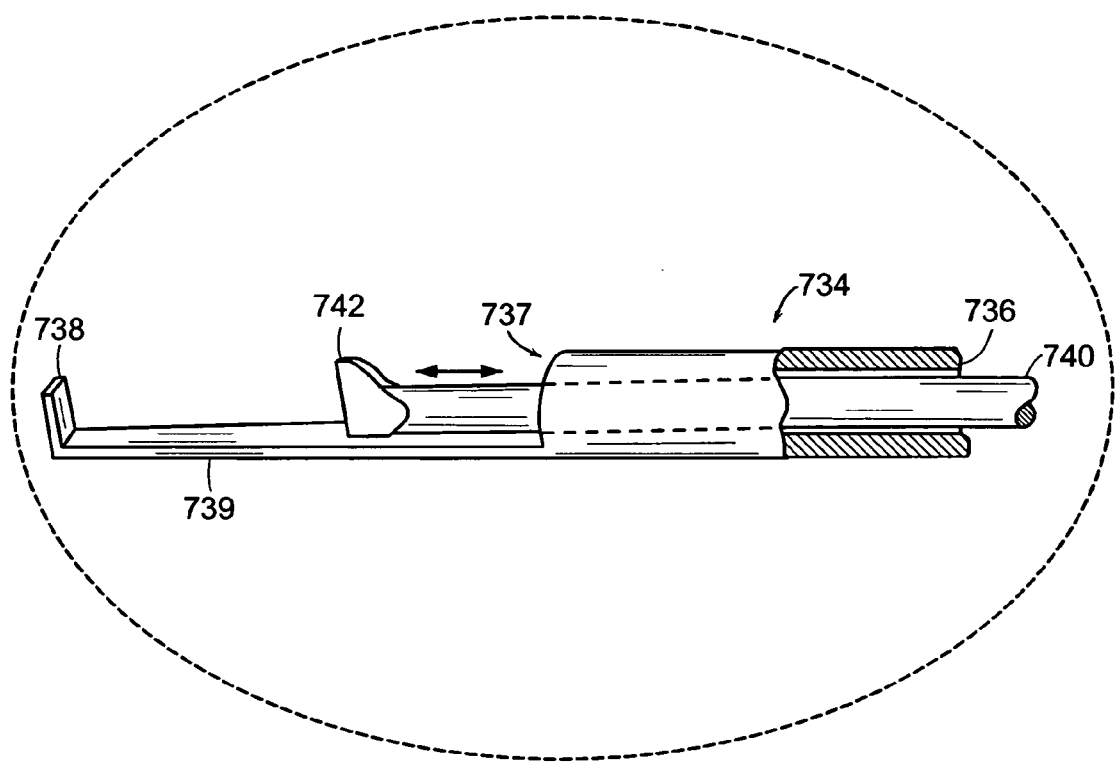
Figure 28:
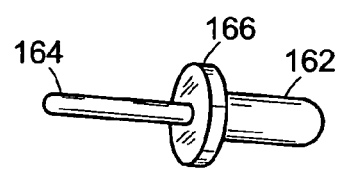
FIG. 28 is a perspective view of a plug for use with an entry alignment devices including a lumen therein.

Now referring to FIGS. 24–25 there are shown various views of a cutting instrument 700 or scissors according to the present invention, that includes a handle member 610 and a head 730, a portion of which is configurable for insertion into the intra-ocular volume. The handle member 610 is described hereinabove in connection with FIGS. 21–23 and as such reference should be made to the foregoing discussion as to the operation and structure of the handle member. The head 730 includes a mechanical interconnecting portion 732, an insertable portion 734 having a lumen 736, and a moveable member 740 having a cutting end 742, that is disposed in the lumen. The insertable portion also includes a fixed end 738 and a bridging portion 739 that extends between an open end 737 of the lumen and the fixed end so as to position the fixed end remote from and opposite the lumen open end.

The mechanical interconnecting portion 732 is affixed to the handle member 610 so the head 730 extends from an end thereof. The mechanical interconnecting portion 732 also is mechanically interconnected to the handle member 610 and the moveable member 740 such that the moveable member moves back and forth axially in the lumen 736 responsive to the axial movement or force generated by the actuation members 612 of the handle member 610. In this way, when the actuation members 612 are in a rest position, the movable member cutting end 742 is remote from the insertable portion fixed end 738 leaving a space therebetween. Correspondingly, when the actuation members 612 are actuated, the moveable member cutting end 742 is moved towards the fixed end 738 so the cutting end contacts the fixed end such that any material disposed between the cutting end 742 and the fixed end 738 is cut or severed into pieces. As illustrated in FIG. 25, the ends of the cutting end 742 and the fixed end 738 that are perpendicular to the line of motion can be further machined or beveled so as to form a pick like surface.

In use, the surgical personnel insert the insertable portion 734 into the entry aperture so the fixed end 738 and lumen open end 737 thereof are dispose in the intra-ocular volume of the eye. Thereafter, the surgical personnel manipulate the cutting instrument 700 so the material to be cut is disposed on the bridging portion 739 between the fixed end 738 and the cutting end 742. The surgical personnel then actuate the actuation members 612 causing the moveable member 740 to moved axially within the lumen towards the fixed end 738 and to urge the cutting end 742 against the fixed end thereby cutting the material trapped therebetween.

The insertable portion 734 is configured and sized so as to be useable with an entry alignment device of the present invention. More particularly, the insertable portion 734 also is configured and sized so the outer diameter or cross-section thereof is sufficiently small such that the removal of the insertable portion from the sclera 6 leaves an incision or opening therein that does not require sutures to seal the opening or incision. In an exemplary embodiment, the outer diameter or cross-section of the insertable portion 734 is about 25 gauge.

Referring now to FIG. 26, there is shown an aspirator 800 according to the present invention that includes a handle portion 802, an insertable member 804 and an suction line 806. The handle member 802 is generally configured so as to provide a shape that is readily grasped by the surgical personnel and to include therein a lumen so as to fluidly couple a lumen of the insertable member 804 and the suction line 806. The suction line 806 is coupled to a suction source (not shown) so as to develop a suction within the insertable member lumen such that material or fluid can be drawn though the open end 808 of the insertable member, up through the lumen and out through the suction line 806 in the same manner as for other prior art aspirators.

The insertable member 804 is configured and sized so as to be useable with an entry alignment device of the present invention. More particularly, the insertable member 804 also is configured and sized so the outer diameter or cross-section thereof is sufficiently small such that the removal of the insertable member from the sclera 6 leaves an incision or opening therein that does not require sutures to seal the opening or incision. In an exemplary embodiment, the outer diameter or cross-section of the insertable member 804 is about 25 gauge.

Figure 27A:
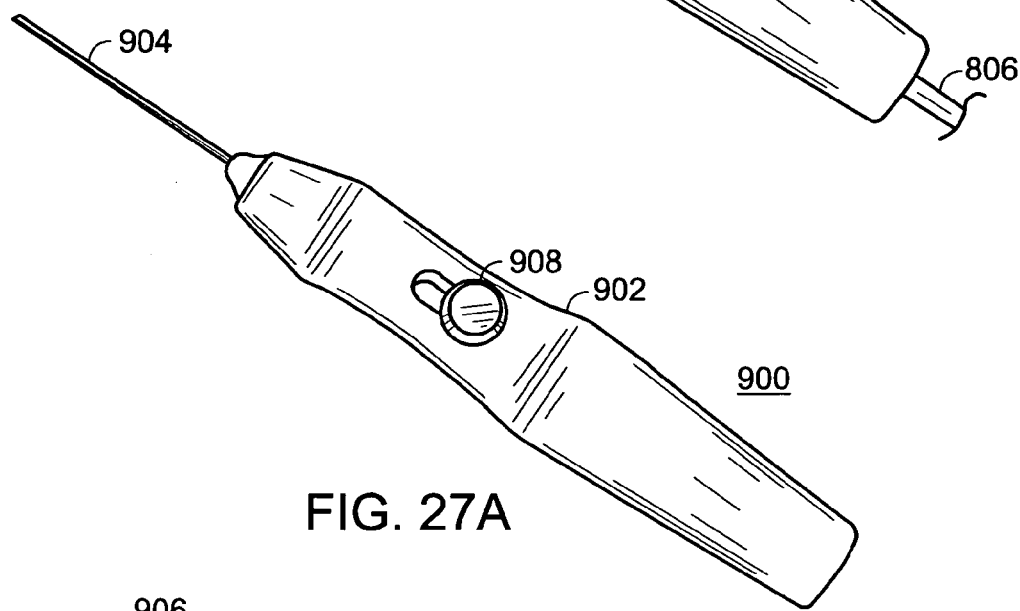
FIG. 27A is a top view of a directional extendable pick according to the present invention, with the pick element in the withdrawn position.
Figure 27B:
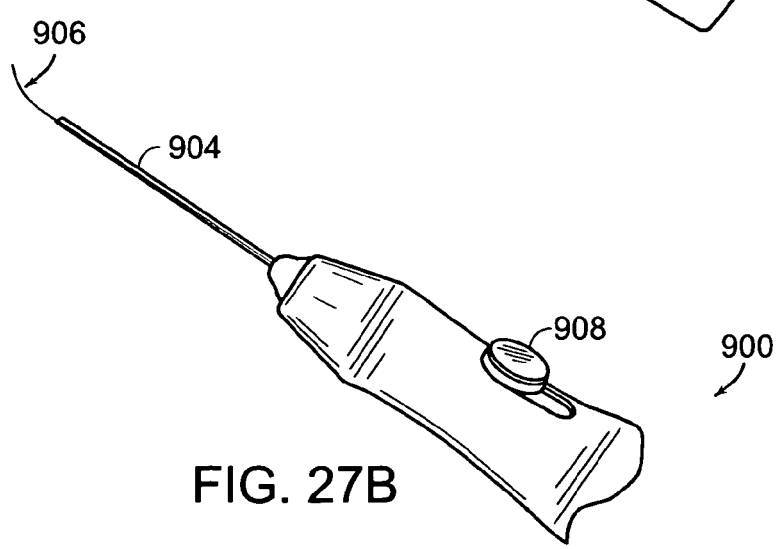
FIG. 27B is a perspective view of the directional extendable pick of FIG. 27A with the pick element in an extended position.

Referring now to FIGS. 27A,B there is shown a directional extendable pick 900 according to the present invention, with the pick portion 906 withdrawn into the insertable portion 904 as shown in FIG. 27A and with the pick portion 906 extending from the insertable portion as illustrated in FIG. 27B. The directional extendable pick 900 includes a handle member 902, the insertable portion 904 that extends from an end of the handle member, a pick portion 906 and a slide member 908 slidably disposed in the handle member. The handle member 902 is generally configured so as to provide a shape that is readily grasped by the surgical personnel.

The insertable portion 904 is configured and arranged with a lumen extending the length thereof in which is slidably disposed the pick portion 906. The handle portion 902 also includes therein a lumen proximal the end from which the insertable portion extends in which is received a segment of the pick portion 906. The handle portion lumen communicates with the slotted opening in the top of the handle portion so the slide member 908 is mechanically connected to the pick portion so that the pick portion moves axially within the insertable portion lumen responsive to the slide member 908.

The pick portion 906 is made of any of a number of materials known in the art that have the rigidity and strength to perform the picking function of the surgical procedure without structurally failing. Such materials include metals such as stainless steel and composite materials such as carbon composites. In a preferred embodiment, the pick portion 906 is made from nitinol. A pick portion 906 made from nitinol is advantageous in that a curved pick portion can be straightened and easily drawn into the straight section of the insertable portion 904, as shown in FIG. 27A, but which returns to the curved state when it is extend outwardly from the insertable portion.

The insertable portion 904 is configured and sized so as to be useable with an entry alignment device of the present invention. More particularly, the insertable portion 904 also is configured and sized so the outer diameter or cross-section thereof is sufficiently small such that the removal of the insertable portion from the sclera 6 leaves an incision or opening therein that does not require sutures to seal the opening or incision. In an exemplary embodiment, the outer diameter or cross-section of the insertable portion 904 is about 25 gauge.

The invention also includes device kits that comprise one or more entry alignment devices 100 according to the present invention with or without the above-described surgical instruments, insertion tools and infusion cannulas. In a more specific embodiment, the device kits include entry alignment devices, a high speed vitreous cutter and an infusion cannula.

Although a preferred embodiment of the invention has been described using specific terms, such description is for illustrative purposes only, and it is to be understood that changes and variations may be made without departing from the spirit or scope of the following claims.

What is claimed is:

1. A method for providing access within an eye during an ocular surgical procedure, comprising the steps of:
    providing an entry alignment device that is configured so as to provide an entry aperture in each of the conjunctiva and sclera of the eye and maintaining the entry aperture in each of the conjunctiva and sclera aligned during the surgical procedure;
    wherein the entry alignment device being provided is sized such that when the entry alignment device is removed from the eye, the entry aperture formed in the conjunctiva and sclera are sealed without the use of sutures;
    inserting the entry alignment device into the eye so as to form the entry apertures, where said inserting is accomplished without pulling back the conjunctiva;
    providing a surgical instrument having an operable end for insertion through the entry aperture in each of the conjunctiva and sclera, a portion of the operable end having a cross-sectional diameter not greater than 25 gauge; and
    inserting the surgical instrument through the entry apertures into the eye.

2. The method according to claim 1, wherein the entry alignment device being provided is sized such that when the entry alignment device is removed from the eye, the entry aperture is self sealing.

3. The method according to any of claims 1 or 2, further comprising the steps of:
    providing a surgical instrument having an operable end for insertion through the entry aperture in each of the conjunctiva and sclera, a portion of the operable end having a cross-sectional diameter not greater than 25 gauge; and
    inserting the surgical instrument through the entry apertures into the eye.

4. The method according to claim 1, wherein the surgical instrument is selected from the group consisting of a high-speed vitreous cutter, forceps, scissors, pick, light source, laser, fragmentation, diathermy, and aspirator.

5. The method according to claim 1, wherein the entry alignment device is in the form of one of a metal cannula, a polyimide cannula, a wire spreader and a shoe-horn type member.

6. The method according to claim 1, wherein there are a plurality of entry alignment devices being provided and wherein the step of inserting includes inserting each of the plurality of entry alignment devices so as to form a plurality of entry apertures in the conjunctiva and the sclera.

7. The method according to claim 6, further comprising the steps of:
    providing a surgical instrument having an operable end for insertion through the entry aperture in each of the conjunctiva and sclera, a portion of the operable end having a cross-sectional diameter not greater than 25 gauge; and
    inserting the operable end portion of at least one surgical instrument through one of the plurality of entry apertures.

8. The method according to claim 1, further comprising the steps of:
    providing an infusion cannula having an operable end for insertion into the eye, the operable end having a cross-sectional diameter of not more than 25 gauge and being interconnected to an infusion source; and
    inserting the cannula operable end through the conjunctiva and sclera.

9. The method according to claim 8, wherein said inserting the infusion cannula further includes inserting the infusion cannula operable end one of directly through the conjunctiva and sclera or through the entry aperture in each of the conjunctiva and sclera formed by the entry alignment device.

10. The method according to claim 8, further comprising the step of sealing the apertures in the conjunctiva and sclera formed by the inserted infusion cannula without the use of sutures.

11. The method according to claim 1, wherein the step of inserting includes inserting the entry alignment device into the eye so the entry apertures in the conjunctiva and sclera are at an angle with respect to a normal to the eye.

12. The method according to claim 11, wherein the angle is greater than 45 degrees from the normal.

13. A method for providing access within an eye during an ocular surgical procedure, comprising the steps of:
    providing an entry alignment device that is configured so as to provide an entry aperture in each of the conjunctiva and sclera of the eye and maintaining the entry aperture in each of the conjunctiva and sclera aligned during the surgical procedure; and
    inserting the entry alignment device into the eye so as to form the entry apertures, where said inserting is accomplished without pulling back the conjunctiva;
    providing an infusion cannula having an operable end for insertion into the eye, the operable end having a cross-sectional diameter of not more than 25 gauge and being interconnected to an infusion source; and inserting the cannula operable end through the conjunctiva and sclera.

14. The method according to claim 13, wherein the entry alignment device being provided is sized such that when the entry alignment device is removed from the eye, the entry aperture formed in the conjunctiva and sclera are sealed without the use of sutures.

15. The method according to claim 13, wherein the entry alignment device being provided is sized such that when the entry alignment device is removed from the eye, the entry aperture is self sealing.

16. The method according to any of claims 2 or 13–15, further comprising the steps of:
    providing a surgical instrument having an operable end for insertion through the entry aperture in each of the conjunctiva and sclera, a portion of the operable end having a cross-sectional diameter not greater than 25 gauge; and
    inserting the surgical instrument through the entry apertures into the eye.

17. The method according to any of claims 2 and 13–15, wherein the surgical instrument is selected from the group consisting of a high-speed vitreous cutter, forceps, scissors, pick, light source, laser, fragmentation, diathermy, and aspirator.

18. The method according to any of claims 2 or 13–15, wherein the entry alignment device is in the form of one of a metal cannula, a polyimide cannula, a wire spreader and a shoe-horn type member.

19. The method according to any of claims 2 or 13–15, wherein there are a plurality of entry alignment devices being provided and wherein the step of inserting includes inserting each of the plurality of entry alignment devices so as to form a plurality of entry apertures in the conjunctiva and the sclera.

20. The method according to claim 19, further comprising the steps of:
    providing a surgical instrument having an operable end for insertion through the entry aperture in each of the conjunctiva and sclera, a portion of the operable end having a cross-sectional diameter not greater than 25 gauge; and
    inserting the operable end portion of at least one surgical instrument through one of the plurality of entry apertures.

21. The method according to any of claims 2 or 13–15, further comprising the step of sealing the apertures in the conjunctiva and sclera formed by the inserted infusion cannula without the use of sutures.

22. The method according to any of claims 2 or 13–15, wherein the step of inserting includes inserting the entry alignment device into the eye so the entry apertures in the conjunctiva and sclera are at an angle with respect to a normal to the eye.

23. The method according to claim 22, wherein the angle is greater than 45 degrees from the normal.

24. The method according to any of claims 2 or 13–15, wherein said inserting the infusion cannula further includes inserting the infusion cannula operable end one of directly through the conjunctiva and sclera or through the entry aperture in each of the conjunctiva and sclera formed by the entry alignment device.

25. A method for treating a posterior segment of an eye comprising the steps of:
    providing a plurality of entry alignment devices, each entry alignment device being configured so as to provide an entry aperture in each of the conjunctiva and sclera of the eye and maintaining the entry aperture in each of the conjunctiva and sclera aligned during the surgical procedure;
    inserting each of the plurality of entry alignment devices into the eye, where said inserting is accomplished without pulling back the conjunctiva; and
    implementing a corrective procedure for the retina.

26. The method of claim 25 wherein said step of implementing further includes
    inserting a light source through the entry aperture formed by one of the plurality of entry alignment devices and inserting a high speed vitreous cutting/aspirating instrument in the entry aperture formed by another of the plurality of entry alignment devices; and
    removing vitreous gel using the high speed vitreous cutting/aspirating instrument.

27. The method of any of claims 26 or 25, further comprising the steps of:
    inserting an operable portion of an infusion cannula through the conjunctiva and the sclera; and
    maintaining the intraocular volume by infusing a fluid through the infusion cannula;
    infusing a first fluid through the infusion cannula while aspirating vitreous fluid; and
    exchanging the infused first fluid with a second fluid following the step of implementing.

28. The method of claim 27, further comprising the steps of:
    infusing a first fluid through the infusion cannula while aspirating vitreous fluid; and
    exchanging the infused first fluid with a second fluid following the step of implementing.

29. The method according to claim 27, wherein said inserting the infusion cannula further includes inserting the infusion cannula operable end one of directly through the conjunctiva and sclera or through the entry aperture in each of the conjunctiva and sclera formed by the entry alignment device.

30. The method according to claim 26, wherein the entry alignment device being provided is sized such that when the entry alignment device is removed from the eye, the entry aperture formed in the conjunctiva and sclera are sealed without the use of sutures.

31. The method according to claim 30, wherein the entry alignment device being provided is sized such that when the entry alignment device is removed from the eye, the entry aperture is self sealing.

32. The method according to claim 30, wherein the entry alignment device is in the form of one of a metal cannula, a polyimide cannula, a wire spreader and a shoe-horn type member.

33. The method according to claim 26, further comprising the steps of:
    providing an infusion cannula having an operable end for insertion into the eye, the operable end having a cross-sectional diameter of not more than 25 gauge and being interconnected to an infusion source; and
    inserting the infusion cannula operable end through the conjunctiva and sclera.

34. The method according to claim 33, further comprising the step of sealing the apertures in the conjunctiva and sclera formed by the inserted infusion cannula without the use of sutures.

35. The method according to claim 33, wherein said inserting the infusion cannula further includes inserting the infusion cannula operable end one of directly through the conjunctiva and sclera or through the entry aperture in each of the conjunctiva and sclera formed by the entry alignment device.

36. The method according to claim 26, wherein the step of inserting includes inserting the entry alignment device into the eye so the entry apertures in the conjunctiva and sclera are at an angle with respect to a normal to the eye.

37. The method according to claim 36, wherein the angle is greater than 45 degrees from the normal.

38. A method for providing access within an eye during an ocular surgical procedure, comprising the steps of:
   providing a plurality of entry alignment device, each entry alignment device being configured so as to provide an entry aperture in each of the conjunctiva and sclera of the eye and maintaining the entry aperture in each of the conjunctiva and sclera aligned during the surgical procedure; and
   inserting each of the plurality of entry alignment device into the eye so as to form a plurality of the entry apertures in the conjunctiva and sclera where said inserting is accomplished without pulling back the conjunctiva.

39. The method according to claim 38, wherein each of the plurality of entry alignment device being provided is sized such that when the entry alignment device is removed from the eye, the entry aperture formed in the conjunctiva and sclera are sealed without the use of sutures.

40. The method according to claim 38, wherein each of the plurality of entry alignment devices being provided is sized such that when the entry alignment device is removed from the eye, the entry aperture is self sealing.

41. The method according to any of claims 38–40, further comprising the steps of:
   providing a surgical instrument having an operable end for insertion through the entry aperture in each of the conjunctiva and sclera, a portion of the operable end having a cross-sectional diameter not greater than 25 gauge; and
   inserting the operable end portion of at least one surgical instrument through one of the plurality of entry apertures.

42. The method according to claim 41, wherein the surgical instrument is selected from the group consisting of a high-speed vitreous cutter, forceps, scissors, pick, light source, laser, fragmentation, diathermy, and aspirator.

43. The method according to any of claims 38–40, wherein each of the plurality of entry alignment devices is in the form of one of a metal cannula, a polyimide cannula, a wire spreader and a shoe-horn type member.

44. The method according to any of claims 38–40, further comprising the steps of:
   providing an infusion cannula having an operable end for insertion into the eye, the operable end having a cross-sectional diameter of not more than 25 gauge and being interconnected to an infusion source; and
   inserting the cannula operable end through the conjunctiva and sclera.

45. The method according to claim 44, further comprising the step of sealing the apertures in the conjunctiva and sclera formed by the inserted infusion cannula without the use of sutures.

46. The method according to claim 44, wherein said inserting the infusion cannula further includes inserting the infusion cannula operable end one of directly through the conjunctiva and sclera or through the entry aperture in each of the conjunctiva and sclera formed by one of the plurality of entry alignment devices.

47. The method according to any of claims 38–40, wherein the step of inserting includes inserting one or more of the plurality entry alignment devices into the eye so the entry apertures in the conjunctiva and sclera are at an angle with respect to a normal to the eye.

48. The method according to claim 47, wherein the angle is greater than 45 degrees from the normal.

* * * * *